United States Patent [19]

Dennis et al.

[11] Patent Number: 5,501,957
[45] Date of Patent: Mar. 26, 1996

[54] METHOD FOR MEASURING GLYCOSYLTRANSFERASE ACTIVITY

[75] Inventors: James W. Dennis, Etobicoike; Katherine A. Siminovitch, Toronto, both of Canada; Alessandro Datti, Terni, Italy

[73] Assignee: Mount Sinai Hospital Corporation, Toronto, Canada

[21] Appl. No.: 293,940

[22] Filed: Aug. 22, 1994

Related U.S. Application Data

[63] Continuation of Ser. No. 968,865, Oct. 30, 1992, abandoned.
[51] Int. Cl.$^6$ .............................. C12Q 1/48; C12Q 1/00; G01N 33/00; A01N 43/04
[52] U.S. Cl. .............................. 435/15; 435/4; 435/14; 435/97; 435/810; 436/94; 436/92; 536/29.11; 536/1.11; 514/54; 514/23; 514/1
[58] Field of Search ................... 435/15, 4, 97, 435/193, 14, 810; 436/89, 92, 94; 536/11, 1.11; 514/54, 23, 1

[56] References Cited

U.S. PATENT DOCUMENTS

| | | | |
|---|---|---|---|
| 4,205,129 | 5/1980 | Podolsky et al. | 435/193 |
| 5,109,126 | 4/1992 | Agrawal et al. | 536/29.11 |
| 5,173,407 | 12/1992 | Vemura et al. | 436/101 |
| 5,352,670 | 10/1994 | Venot et al. | 514/54 |

FOREIGN PATENT DOCUMENTS

| | | |
|---|---|---|
| 0134292 | 3/1985 | European Pat. Off. |
| 0272603 | 6/1988 | European Pat. Off. |
| 0387875 | 9/1990 | European Pat. Off. |

OTHER PUBLICATIONS

Verdon and Berger, Methods of Enzymatic Analysis, 3:374–381, 1986.
Rademacher, T. W. et al, Ann. Rev. Biochem. 57:785, 1988.
Yousefi, S. et al, J. Biol. Chem. 266:1772, 1991.
Dennis, J. W. et al, Science, vol. 236, pp. 582–585, 1987.
Warren L. et al. Biochem. Biophys. Acta. 516:97, 1978.
Piller, F. et al, J. Biol. Chem. 263:15146, 1988.
Higgins, L. A. J. Biol. Chem. 266:6280, 1991.
Brockhausen, I. et al Cancer Res. 51:1257, 1991.
Paulson, J. C. et al J. Biol. Chem. 264, pp. 10931–10934, 1989.
Wang, X et al Glycobiology 1:25, 1990.
Nishikawa et al J. Biol Chem. 263; 8270–8281, 1988.
M. G. Shoreibah et al J. Biol. Chem. 267: 2920–2927:1992.
Schanbacher and Ebner, J. Biol. Chem. 245:5057–5061, 1970.
Yoon and Laine, Glycobiology 2:161–168, 1992.
Holt, G. D. et al J. Cell. Biol. 104:1157, 1987.
Viitala, J. and Finne, J. Eur. J. Biochem. 138:393, 1984
Cornil, I. et al, J. Cell Biol. 111:773, 1990.
Williams and Schachter, (1980) J. Biol. Chem. 255:11247.
Williams et al (1980) J. Biol. Chem. 255:11253.
Schacter et al. (1971) J. Biol. Chem. 246:5321.
Greer et al., Biochem. Cell Biol., vol. 67, pp. 503–509, 1989.
Thrope et al., Development, 102:193–210, 1988.

*Primary Examiner*—Michael G. Wityshyn
*Assistant Examiner*—Louise N. Leary
*Attorney, Agent, or Firm*—Bereskin & Parr

[57] ABSTRACT

A method of assaying for glycosyltransferase activity in a sample. In a first step, a sample is reacted with a first sugar donor and an acceptor substrate to produce a transferase product. The first sugar donor and acceptor substrate are selected such that the sugar from the first sugar donor is capable of being transferred to the acceptor substrate in the presence of the glycosyltransferase to be assayed. In a second step, the transferase product is reacted with a second sugar donor having a sugar which is labelled with a labelling agent and an enzyme which is capable of transferring the sugar from the second sugar donor to the transferase product to produce a labelled transferase product and which has a higher affinity for the glycosyltransferase product compared to the affinity of the glycosyltransferase for the acceptor substrate. The labelling agent activity of the labelled transferase product or unreacted second sugar donor is assayed to determine transferase activity in the sample. A kit for assaying for glycosyltransferase activity in a sample is also described.

28 Claims, 14 Drawing Sheets

A

B

A

B

A

B

A

B

METHOD FOR MEASURING GLYCOSYLTRANSFERASE ACTIVITY

This application is a continuation of Ser. No. 07/968,865, filed Oct. 30, 1992, now abandoned.

FIELD OF THE INVENTION

The invention relates to a method for assaying glycosyltransferase activity, use of the method for diagnosing conditions involving aberrant glycosyltransferase activity, and a kit for assaying for glycosyltransferase activity.

BACKGROUND OF THE INVENTION

Cell surface oligosaccharides are known to play a crucial role in mediating cell-cell interactions in development and in the disease state. The developmentally-regulated patterns of glycoprotein glycosylation are determined largely by the activity and specificity of glycosyltransferase enzymes expressed in the Golgi (Rademacher, T. W. et al, Ann. Rev. Biochem. 57:785, 1988; and Yousefi, S. et al, J. Biol. Chem. 266:1772, 1991). Changes in glycosyltransferase activities have been associated with malignancies and other disease conditions, although the factors and intracellular signalling pathways which regulate expression of glycosyltransferase activities in the Golgi are largely unknown.

Several disease states are known to be associated with expression of specific glucosaminyltransferases resulting in altered patterns of cellular oligosaccharides. For example, the modification of cell surface carbohydrates has been linked to transformation and metastasis (Dennis, J. W. et al, Science, 1987). Malignant transformation of murine and human cells is commonly associated with expression of the larger complex N-linked oligosaccharides and increased polylactosamine content (Warren, L. et al. Biochem. Biophys. Acta. 516:97, 1978). Recent evidence suggests that the branching, extension and polylactosamine content of O-linked oligosaccharides may also affect metastasis or tumor growth (Yousefi S. et al, J. Biol. Chem. 266:1772, 1991).

The Golgi enzyme UDP-GlcNAc:Galβ1-3GalNAc-R β1-6-N-acetylglucosaminyltransferase, D-N-acetylglucosamine to D-N-acetylgalactosamine, (GlcNAc to GalNAc) (core 2 GlcNAc-T) substitutes "core 1" O-linked glycans (i.e., Galβ1-3GalNAcα) to produce "core 2" structures (i.e., fold Galβ1-3GalNAcβ1-6GlcNAcα). UDP-Gal: GlcNAC-R β1-4-galactosyltransferase. β1-4Gal-T subsequently acts on core 2 producing β1-6 linked lactosamine which can be extended into polylactosamine by UDP-GlcNAc:Galβ4GlcNAc-Rβ3-N-acetylglucosaminyl (β1-3GlcNAc-T(i) and β1-4Gal-T. Core 2 GlcNAc-T activity appears to be an important rate limiting step in the extension of O-linked oligosaccharides with polylactosamine (i.e., repeating Galβ1-4GlcNAcβ1-3), a structure which has been associated with malignant transformation (Yousefi et al, J. Biol. Chem. 266:1772, 1991).

Changes in the activity of core 2 GlcNAc-T have also been associated with the Wiskott-Aldrich immunodeficiency syndrome (WAS). Increased core 2 GlcNAc-T activity is closely associated with activation of human T cells in vitro, via the T cell receptor complex (Piller, F. et al, J. Biol. Chem. 263:15146, 1988). Furthermore, lymphocytes of patients with WAS show abnormal regulation of the enzyme (Higgins, L. A. J. Biol. Chem. 266:6280, 1991).

Core 2 GlcNAc-T activity appears to be regulated by factors which have an impact on intracellular signalling and developmental status of the cell. For example, T cell activation via the T cell receptor complex in vitro is associated with a 3 fold increase in core 2 GlcNAc-T activity (Piller, F. et al, J. Biol. Chem. 263:15146, 1988; and Higgins, L. A. et al, J. Biol. Chem. 266:6280, 1991). Lymphocytes from patients with WAS show both abnormal proliferative responses and abnormal regulation of core 2 GlcNAc-T. Enzyme activity is increased following transformation of rat 2 fibroblasts and murine mammary carcinoma cells by activated H-ras (Yousefi, S. et al., J. Biol. Chem. 266:1772, 1991), in human leukemias (Brockhausen, I. et al Cancer Res. 51:1257, 1991).

Tissue-specific patterns of oligosaccharide processing may be regulated at both the level of transcription of glycosyltransferase genes and post-translational modifications of their protein products. For example, recent studies of α2-6SA-T showed that mRNA levels varied between tissues by as much as 50 fold, correlating with tissue specific differences in enzyme activity (Paulson, J. C. et al J. Biol. Chem. 264, 1989). Tissue-specific regulation of glycosyltransferases may also take the form of alternate mRNA splicing, or alternate translation initiation and termination signals allowing production of multiple proteins, possibly with different activities or acceptor specificities. In this regard, 5 exons of the rat α2-6SA-T gene are present in liver transcripts while only 3 of these exons are present in kidney mRNA. The hepatic SA-T mRNA is transcribed from the first exon, while the kidney transcript is initiated from a promoter and ATG codon within the third intron (Wang, X et al Glycobiology 1:25, 1990). Tissue-specific promoter elements have also been identified in the rat α2-6SA-T gene which appear to control expression of the enzyme in both tissues (Paulson, J. C. et al., J. Biol. Chem. 264, 1989).

Studies of the role of glucosaminyltransferases in the oncodevelopmental and disease process have been limited by the lack of highly sensitive and specific assays for the individual transferase enzymes. Assays for glycosyltransferases have involved reacting a sugar nucleotide donor which is labelled with $^3H$ or $^{14}C$ and subsequently measuring the radioactivity of the acceptor to which the labelled sugar is transferred by the glycosyltransferase. Morito, in European Patent Application number 87118665.6, discloses a method for measuring glycosyltransferase using a constitution containing a donor which is not labelled and a substance which is specifically bound only to a product.

SUMMARY OF THE INVENTION

The present inventors have developed a sensitive and specific method to assay for glycosyltransferase activity. In the first step of the method, a sample suspected of containing a glycosyltransferase is reacted with an acceptor substrate and a sugar donor. If the glycosyltransferase is present in the sample, the sugar is transferred to the acceptor substrate to produce a transferase product. In the second step, the transferase product is reacted with a second sugar donor and an enzyme which transfers the second sugar to the transferase product. The enzyme used in the second step is selected such that it has a lower Km and accordingly a higher affinity for its substrate compared to the glycosyltransferase to be assayed.

In particular, the inventors have developed a method to assay for core 2 GlcNAc-T activity using purified bovine β1-4Gal-T and UDP-[$H^3$]Gal to label the core 2 reaction product. A comparison of the coupled core 2 GlcNAc-T assay and a single step assay using UDP-[$H^3$]Gal and UDP-[$^3H$]GlcNAc with similar specific activities, respectively, showed that the former assay is approximately 100 times more sensitive than the standard assay using UDP-[$^3H$]GlcNAc as a sugar donor. Core 2 GlcNAc-T reactions were performed using unlabeled UDP-GlcNAc donor and Galβ1-3GalNAcα-paranitrophenyl (pNp) as acceptor. The product, Galβ1-3(GlcNAcβ1-6)GalNAcα-pNp was then further reacted with purified bovine β1-4Gal-T and UDP-[$^3H$]Gal to produce Galβ1-3([$^3H$]Galβ1-4GlcNAcβ1-6)GalNAcα-pNp. Approximately 10% of the available GlcNAc-terminating acceptor was substituted in the Gal-T reaction, and allowed 1 picomoles of product to be readily detected. The increased sensitivity of the coupled assay facilitates studies of core 2 GlcNAc-T activity where material is limiting, or specific activity is low.

The following reaction scheme for a coupled assay for assaying for core 2 GlcNAc-T is illustrative of the method of the invention:

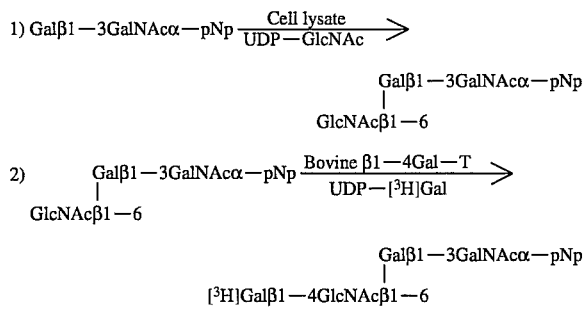

Broadly stated the invention relates to a method of assaying for glycosyltransferase activity in a sample, which comprises reacting the sample with a first sugar donor and an acceptor substrate to produce a transferase product, the first sugar donor and acceptor substrate being selected such that the sugar from the first sugar donor is capable of being transferred to the acceptor substrate in the presence of the glycosyltransferase to be assayed, reacting the transferase product with a second sugar donor having a sugar which is labelled with a labelling agent and an enzyme which is capable of transferring the sugar from the second sugar donor to the transferase product to produce a labelled transferase product and which has a higher affinity for the transferase product compared to the affinity of the glycosyltransferase for the acceptor substrate, and assaying for the labelling agent activity of the labelled transferase product or unreacted second sugar donor.

The first sugar donor and the second sugar donor are preferably nucleotide sugar donors. The acceptor substrate preferably has an oligosaccharide portion and a linker group. In one embodiment the enzyme is β1-4 Gal-T and the second sugar donor is a nucleotide sugar donor comprising Gal labelled with a labelling agent, preferably UDP-Gal.

The labelling agent which may be used in the method of the invention may be an enzyme, fluorescent substance, radioactive substance, or chemiluminescent substance.

The method of the invention may be used to assay for glucosaminyltransferases including the following: UDP-GlcNac:Galβ3GalNAc-R β6-N-acetylglucosaminyltransferase; UDP-GlcNAc:GalNAc-R β3-N-acetylglucosaminyltransferase; UDP-GlcNAc:α3Man β2-N-acetylglucosaminyltransferase I; UDP-GlcNAc:Gal β4GalNAc-R β3-N-acetylglucosaminyltransferase; UDP-GlcNAc:Galβ3GalNAc-R β3-N-acetylglucosaminyltransferase; UDP-GlcNAc: dolichol diphospho N-acetylglucosamine β1-4 N-acetylglucosaminyltransferase; UDP-GlcNAc:Galβ1-3GlcNAc-R β1-3 N-acetylglucosaminyltransferase; UDP-GlcNAc:Galβ1-4GlcNAc-R β1-6 N-acetylglucosaminyltransferase; or UDP-GlcNAc:Galβ1-4Glc β-R β1-3 N-acetylglucosaminyltransferase. The method of the invention may also be used to assay for glucosyltransferases.

In a particularly preferred embodiment of the invention the method of the invention is used to assay for UDP-GlcNac:Galβ3GalNAc-R β6-N-acetylglucosaminyltransferase and the acceptor substrate comprises Galβ1-3GalNAcα-pNp, the first sugar donor is a nucleotide sugar donor, preferably UDP-GlcNAc, the enzyme is β1-4 Gal-T and the second sugar donor is a nucleotide sugar donor comprising Gal labelled with a labelling agent, preferably UDP-Gal.

The method of the invention may be used for the diagnosis of conditions associated with aberrant glycosyltransferase activity such as immunodeficiency diseases, cancer, and lysosomal storage diseases.

The present invention also provides a kit for assaying for glycosyltransferase activity in a sample comprising a first sugar donor and an acceptor substrate, the first sugar donor and acceptor substrate being selected such that the sugar portion of the first sugar donor is capable of being transferred to the acceptor substrate in the presence of the glycosyltransferase to be assayed to produce a transferase product, a second sugar donor having a sugar portion which is labelled with a labelling agent, an enzyme which is capable of transferring the sugar portion from the second sugar donor to the transferase product to produce a labelled transferase product and which has a higher affinity for the transferase product compared to the affinity of the glycosyltransferase for the acceptor substrate, and means for detecting the labelling agent activity of the labelled transferase product or unreacted second sugar donor.

The kit may be used to assay for glucosaminyltransferases such as UDP-GlcNac:Galβ3GalNAc-R β6-N-acetylglucosaminyltransferase; UDP-GlcNAc:GalNAc-R β3-N-acetylglucosaminyltransferase; UDP-GlcNAc:α3Man β2-N-acetylglucosaminyltransferase I; UDP-GlcNAc:Gal β4GalNAc-R β3-N-acetylglucosaminyltransferase; UDP-GlcNAc:Galβ3GalNAc-R β3-N-acetylglucosaminyltransferase; UDP-GlcNAc: dolichol diphospho N-acetylglucosamine β1-4 N-acetylglucosaminyltransferase; UDP-GlcNAc:Galβ1-3GlcNAc-R β1-3 N-acetylglucosaminyltransferase; UDP-GlcNAc:Galβ1-4GlcNAc-R β1-6 N-acetylglucosaminyltransferase; or UDP-GlcNAc:Galβ1-4Glc β-R β1-3 N-acetylglucosaminyltransferase. The kit may also be used to assay for glucosyltransferases.

In a preferred embodiment of the invention a kit is provided for assaying UDP-GlcNac:Galβ3GalNAc-R β6-N-acetylglucosaminyltransferase activity in a sample, comprising an acceptor substrate comprising Galβ1-3GalNAcα-pNp and a first sugar donor having a GlcNAc sugar portion which is transferred to the acceptor substrate in the presence of UDP-GlcNac:Galβ3GalNAc-R β6-N-acetylglucosaminyltransferase and to produce a transferase product; UDP-Gal wherein Gal is labelled with a labelling agent and β1-4 Gal transferase for transferring labelled Gal to the transferase product to produce a labelled transferase product, and means for detecting the labelling agent activity of the labelled transferase product or unreacted labelled UDP-Gal to determine the UDP-GlcNac:Galβ3GalNAc-R β6-N-acetylglucosaminyltransferase activity. The kit may further comprise means for comparing the UDP-GlcNac:Galβ3GalNAc-R β6-N-acetylglucosaminyl-transferase activity in samples from a normal patient and a patient with a condition associated with aberrant UDP-GlcNac:Galβ3GalNAc-R β6-N-acetylglucosaminyltransferase activity, for example, immunodeficiency diseases such as Wiskott-Aldrich immunodeficiency syndrome (WAS), lysosomal storage diseases and cancer.

DESCRIPTION OF THE DRAWINGS

The invention will be better understood with reference to the drawings in which.

DETAILED DESCRIPTION OF THE INVENTION

Figure 1:
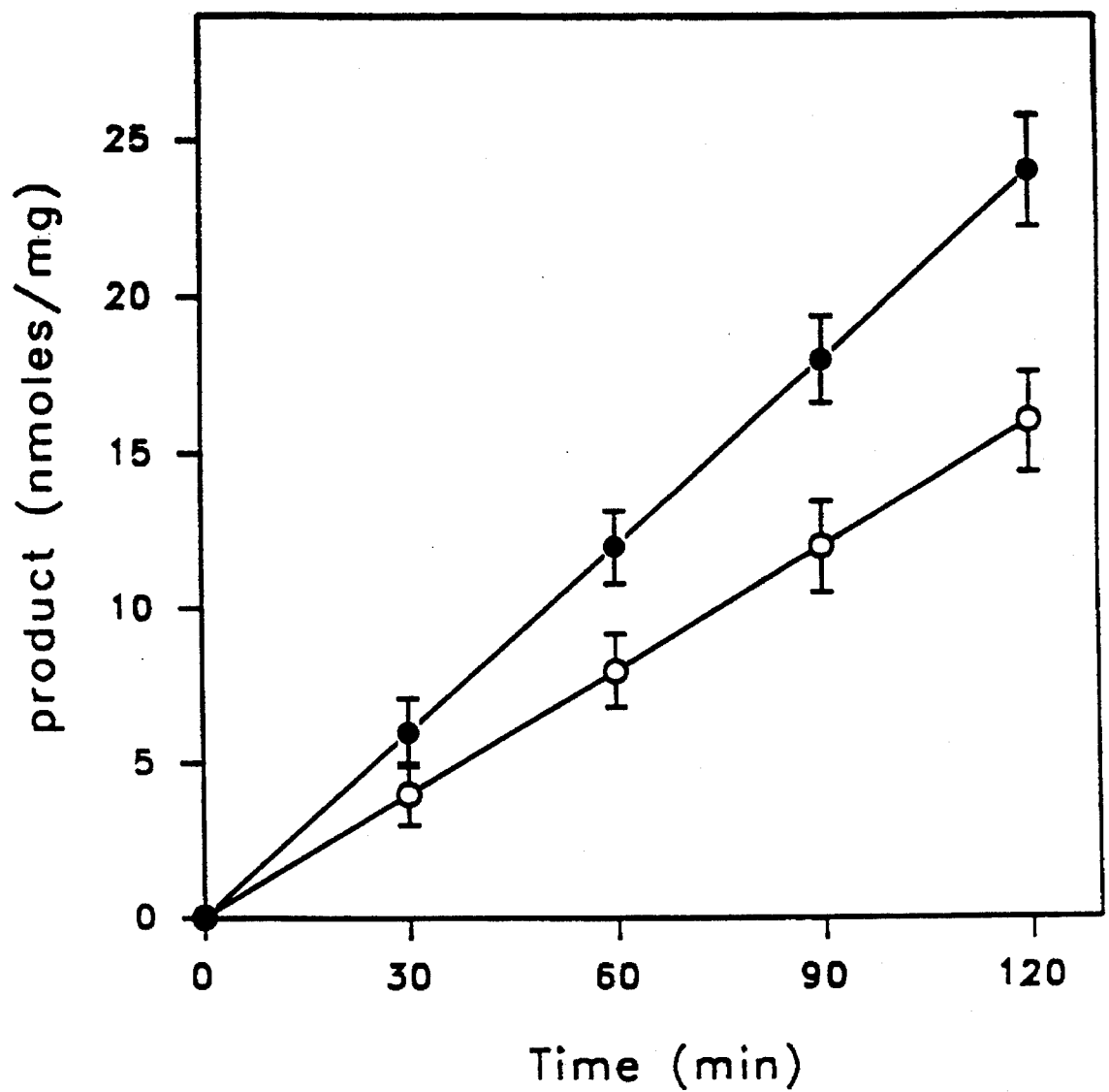
FIG. 1 is a graph showing core 2 GlcNAc-T measured in MDAY-D2 cell lysate as a function of reaction time, at 30° C. (○), or 37° C. (●).

As hereinbefore mentioned, the invention relates to a method of assaying for glycosyltransferase activity in a sample, which comprises reacting the sample with a first sugar donor and an acceptor substrate to produce a transferase product, the first sugar donor and acceptor substrate being selected such that the sugar from the first sugar donor is capable of being transferred to the acceptor substrate in the presence of the glycosyltransferase to be assayed, reacting the transferase product with a second sugar donor having a sugar which is labelled with a labelling agent and an enzyme which is capable of transferring the sugar from the second sugar donor to the transferase product to produce a labelled transferase product and which has a higher affinity for the transferase product compared to the affinity of the glycosyltransferase for the acceptor substrate, and assaying for the labelling agent activity of the labelled transferase product or unreacted second sugar donor.

The method of the invention may be adapted for glucosyltransferases or glucosaminyltransferases where the transferase product has a single GlcNAc or glucose (Glu) terminus, respectively. It is expected that glucosyltransferases and glucosaminyltransferases which exhibit similar kinetics to core 2 GlcNAc-T and which have lower affinities for an acceptor substrate than the enzyme utilized in the second reaction step, may be assayed using the method of the invention. Glycosaminyltransferases generally have less favorable Km values than β1-4 Gal-T, particularly for their natural substrates (Nishikawa et al J. Biol Chem. 263; 8270–8281, 1988; M. G. Shoreibah et al J. Biol. Chem. 267: 2920–2927:1992) and therefore it is expected that glucosaminyltransferases can be assayed with enhanced sensitivity by the coupled assay method described herein.

Examples of glycosyltransferases which may be assayed by the coupled assay of the invention are shown in Table 1. For example, β1-3GlcNAc-T(i) could be assayed in the manner described herein using Galβ1-4GlcNAcβ1-6Manα1-6Glc-aglycan as acceptor substrate. Preferably, core 2 GlcNAc-T activity is assayed using the method of the invention. Glucosyltransferases include conjugating enzymes for elimination of hydrophobic compounds from the body having substrates including natural products, toxins, drugs and their metabolites. Examples of glucosyltransferases which may be assayed using the method are α-glucosidase and β-glucosidase.

The first sugar donor and acceptor substrate are selected such that the sugar from the first sugar donor is transferred to the acceptor substrate in the presence of the glycosyltransferase to be assayed. Accordingly, the acceptor substrate selected is dependent upon the glycosyltransferase to be assayed. Table 1 lists examples of glycosaminyltransferases that may be assayed using the method of the invention and examples of suitable minimal substrates. The acceptor substrate has an oligosaccharide portion and it may be an oligosaccharide, a glycopeptide or a glycoprotein either synthetic or a naturally occurring structure. The minimal structure for the oligosaccharide portion may be the appropriate substrate for example as shown in Table 1, with or without a linker group at the reducing end. A linker group is any group which does not interfere with the activity of the glycosyltransferase to be assayed and includes hydrophobic aglycon groups such as pNp or (CH$_2$)$_8$—COOH$_3$, an oligosaccharide, lipid, phenyl, aryl, or alkyl group. The linker group may also be a carrier such as sepharose as more particularly described herein, to produce an insolubilized acceptor substrate. The linker group may be attached to the oligosaccharide portion in the appropriate anomeric configuration. Preferably the linker group is selected such that it enhances enzyme activity and specificity. Derivatives or analogues of the acceptor substrates, for example, derivatives where hydroxyl(s) are removed or substituted by, for example, halogen or phenol, may also be used in the method of the invention.

The first sugar donor has a sugar portion and a portion which is recognised by the glycosyltransferase to be assayed. The sugar portion is selected depending on the glycosyltransferase to be assayed. If a glucosyltransferase is to be assayed the sugar is glucose and if a glucosaminyltransferase is to be assayed the sugar is GlcNAc. Functional and structural analogues of the sugars may be used in the method of the invention. For example, sugars where the hydroxyl groups are deleted or substituted may be used in the method of the invention. The portion which is recognised by the glycosyltransferase to be assayed may be a nucleotide, preferably UDP or an oligosaccharide. In a preferred embodiment for assaying for core 2 GlcNAc, the sugar donor is UDP-GlcNAc or a derivative of UDP-GlcNAc wherein the hydroxyl groups of GlcNAc are deleted or substituted.

The enzyme is capable of transferring the labelled sugar portion from the second sugar donor to the transferase product and it has a higher affinity for the transferase product compared to the affinity of the glycosyltransferase for the acceptor substrate. Preferably the enzyme is a Glc or Gal transferase. In a preferred embodiment the enzyme is β1-4 Gal-T, such as natural or recombinant β1-4 Gal-T, most preferably bovine β1-4 Gal-T. In a particularly preferred embodiment β1-4 Gal-T (E.C. 2.4.1.38) is used. β1-4 Gal-T (E.C. 2.4.1.38) is highly specific for transfer of Gal to GlcNAc. Acceptor specificity of this enzyme is converted to glucose by the addition of the co-factor α-lactalbumin, and the activity of this complex is designated E.C. 2.4.1.22. (Schanbacher and Ebner, J. Biol. Chem. 245:5077–5061, 1970; Yoon and Laine, Glycobiology 2:161–168, 1992). Accordingly, E.C. 2.4.1.22 may be used in the method of the invention where the terminus of the transferase product is glucose.

The use of relatively high concentrations of β1-4Gal-T enzyme appears to increase the sensitivity of the preferred method of the invention for assaying core 2 GlcNAc-T. In addition, sensitivity is enhanced due to the favourable substrate Km values for β1-4Gal-T, which are lower than that for the core 2 GlcNAc-T enzyme in CHO and MDAY-D2 cell lysates (Youseffi, S. et al, J. Biol. Chem. 266, 1772–1783, 1991).

Bovine β1-4Gal-T has been used in studies on oligosaccharide structure and function in other experimental systems. For example, β1-4Gal-T has been used to identify unsubstituted GlcNAc attached to ser/thr of cytosolic and nuclear proteins (ie. O-linked GlcNAc) (Holt, G. D. et al J. Cell. Biol. 104:1157, 1987). Following endo β-galactosidase-treatment, β1-4Gal-T has been used to identify and quantitate polylactosamine sequences (Youseffi, S. et al, J. Biol. Chem. 266:1772, 1991; and Viitala, J. and Finne, J. Eur. J. Biochem. 138:393, 1984). The enzyme has also been used to restore Gal to N-linked oligosaccharides on the surface of mutant tumor cells which are deficient in UDP-Gal transport into the Golgi. The addition of β1-4 linked Gal has also been found to enhance tumor cell adhesion to endothelial cells in vitro and organ colonization by the cells in vivo (Cornil, I. et al, J. Cell Biol. 111:773, 1990).

The second sugar donor is anything that efficiently transfers the sugar to the enzyme. The second sugar donor comprises a sugar portion and a portion which is recognised by the enzyme. The sugar is selected depending on the enzyme used in the method. For example, if a Gal transferase is used as the enzyme the sugar portion is galactose. Functional and structural analogues of the sugars may be used in the method of the invention. For example, sugars where the hydroxyl groups are deleted or substituted may be used in the method of the invention. The portion which is recognised by the glycosyltransferase to be assayed may be an oligosaccharide or a nucleotide, preferably UDP. In a preferred embodiment for assaying for core 2 GlcNAc, where the enzyme is Gal transferase, the sugar donor is UDP-Gal or a derivative of UDP-Gal wherein the hydroxyl groups of Gal are deleted or substituted.

The sugar portion of the second sugar donor may be labelled with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive tritium. Fluorescent labelled second sugar donor may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin. In a preferred embodiment the labelled second sugar donor is UDP[$^3$H]Gal. Conventional methods may be used to label the sugar portion of the second sugar donor.

The method of the invention may be used to assay glycosyltransferase activity in a wide range of samples, wherever the glycosyltransferase occurs. Any biological sample may be used and the sample may be from an animal or plant which possesses the glycosyltransferases. Plant samples may be obtained from any plant tissue containing Golgi, including stem, leaves and roots. Animal and human samples may be obtained from biological fluids, such as saliva, serum, urine, from tissue or cell samples, cell cultures or cell lines. Examples of suitable samples to be used in the method of the invention are discussed below.

A tissue section, for example, a freeze-dried or fresh frozen section of tissue removed from a subject may also be used as the sample for determination of glycosyltransferase activity. As to details relating to the general techniques of preparing tissue sections, reference may be made to general text books, for example, A. G. Everson Pearce, Histochemistry Theoretical and Applied, 4th Ed., Churchill Livingstone, Edinburgh, 1980.

A cell lysate fraction can be separated from a tissue sample removed from a patient and can be used as a sample for the determination of glycosaminyltransferase activity. Conventional methods can be used to separate out a cell lysate fraction. More specifically, the desired cell lysate fraction can be prepared by suspending the tissue sample in 10 mM Tris-HCl pH 7.4, 0.9% NaCl, 1 mM PMSF and 0.1% aprotinin homogenized using a Polytron homogenizer. After centrifugation the membrane pellet may be solubilized in 1% Triton X-100, 40 mM sodium cacodylate, pH 7.0 and nuclei and debris may be removed by centrifugation.

A protein fraction may be separated from a crude sample and may be used as the sample for the determination of glycosyltransferase activity. Conventional methods such as precipitation, electrophoresis, affinity chromatography, gel filtration and immunoprecipitation can be used to separate out a protein fraction.

It will be appreciated that the sensitivity and specificity of the method of the invention permits measurement of glycosyltransferase activity in crude homogenates or fractions of the above-noted samples. The improved sensitivity and specificity of the method of the invention also makes it particularly advantageous where sample material is limited, for example, in infant patients suspected of having WAS.

The method of the invention may be used in the diagnosis of conditions associated with aberrant glycosyltransferase activity. Accordingly, where the method of the invention is used to diagnose cancer, tumor tissue removed from a patient can be used as the sample. In order to prevent tumor samples from being denatured, the samples may be stored at temperatures below −20° C. Other compounds which may be added to tumor samples are sucrose and glycerol. A tissue section, for example, a freeze-dried or fresh frozen section of tumor tissue removed from a patient can also be used as the tumor sample for determination of glycosyltransferase activity.

Suitable samples for the detection of WAS by the method of the invention may be obtained from the peripheral blood of WAS or normal patients. In a preferred embodiment samples enriched in T-lymphocytes or platelets may be prepared from peripheral blood samples.

Peripheral blood samples may be collected in heparinized containers and fractions enriched in T-lymphocytes or platelets may be prepared by methods known in the art. For example mononuclear cells and platelets may be isolated by density gradient centrifugation, and macrophages depleted by allowing them to adhere to plastic. In an embodiment of the invention the coupled assay may be carried out on samples of activated T lymphocytes. T lymphocytes may be activated, for example by incubation with ant-CD3 antibody, interleukin-2, WT32 or leukoagglutinin.

The samples to be assayed may be stored and enzymatic activity may be preserved by methods known in the art such as freezing and lyophilisation.

The method of the invention is carried out by mixing a predetermined amount of a sample with a first sugar donor and an acceptor substrate. The appropriate reaction conditions may be selected depending on the glycosyltransferase to be assayed and sugar donor present in the reaction. The sample is reacted with the acceptor substrate and first sugar donor for a sufficient period and at a pH and temperature effective for the glycosyltransferase to interact with the first sugar donor and acceptor substrate to produce the transferase product. The sample is incubated with the first sugar donor and an acceptor substrate for approximately 5 minutes to 5 hours, preferably 1 to 2 hours. The acceptor substrate and first sugar donor are effective to interact with the glycosyltransferase to be assayed within wide pH and temperature ranges, for example from about pH 5 to 8 and from about 20° to 45° C., preferably from 37° C. The amount of first sugar donor and acceptor substrate used in the method is dependent upon the glycosyltransferase to be measured. For example, the first sugar donor may be present in an amount of at least 2×Km of the glycosyltransferase to be assayed, preferably 2–20 mM, most preferably 4 mM. The acceptor substrate may be present in an amount of at least 2×Km of the glycosyltransferase to be assayed, preferably 2–10 mM, most preferably 2 mM. The amount of protein in the sample may be in the range from 1–1,000 ug.

It is preferred to use a buffer with the acceptor substrate and first sugar donor. Suitable buffers are well known in the art, for example MES, TES, HEPES and Tris. The buffer and acceptor substrate together can be used as an assay composition. A buffer is present in such a composition to maintain the pH within the pH range effective for glycosyltransferase activity. Divalent cations, such as $Ca^{2+}$, $Mg^{2+}$ or $Mn^{2+}$ may be present. Detergents may be added to the assay composition.

The resulting transferase product may be isolated by conventional isolation techniques, for example, salting out, chromatography, electrophoresis, gel filtration, fractionation, absorption, polyacrylamide gel electrophoresis, agglutination, or combinations thereof preferably using an HPLC column such as an Ultrahydrogel HPLC column (Waters), carbohydrate column or amino column.

The acceptor substrate may be insolubilized, for example, the acceptor substrate can be reacted using known chemical or physical methods with a suitable carrier. The carrier may be selected based on the nature of the acceptor substrate. It will also be appreciated that the carrier may be a linker group attached to the oligosaccharide portion of the acceptor substrate. Examples of suitable carriers are Sepharose, agarose beads, cellulose, dextran, Sephadex, carboxymethyl cellulose polystyrene, filter paper, ion-exchange resin, plastic film, plastic tube, glass beads, polyamine-methyl vinylether-maleic acid copolymer, amino acid copolymer, ethylene-maleic acid copolymer, nylon, silk, etc. The carrier may be in the shape of, for example, a tube, test plate, beads, disc, sphere etc. When an insolubilized acceptor substrate or sample is used unreacted material such as unreacted first sugar donor may be removed by washing with a buffer, for example, phosphate buffered saline (PBS) with bovine serum albumin (BSA).

In the second step of the method of the invention, the transferase product is mixed with a predetermined amount of a second sugar donor having a labelled sugar and an enzyme which is capable of transferring the labelled sugar to the transferase product to produce a labelled transferase product. The transferase product is incubated with the second sugar donor and the enzyme for a sufficient time to saturate the transferase product. Typically the incubation time is from 2 seconds to 24 hours, most preferably 2 hours. The second sugar donor and enzyme are effective to interact with the transferase product within wide pH and temperature ranges, for example from about pH 5 to 8 and from about 20° to 45° C., preferably from 30° C. The amount of second sugar donor and enzyme used in the method is sufficient to provide a signal and is dependent on the labelling agent used to label the sugar portion of the second sugar donor and glycosyltransferase to be assayed. The second sugar donor should be present in sufficient amounts to saturate the substrate i.e. transferase product. For example, if UDP-[$^3$H] Gal is used as the second sugar donor it may be present in an amount of 0.1 mM to 10 mM, preferably 1 mM.

It is preferred to use a buffer with the second sugar donor and the enzyme. A buffer is present in such a composition to maintain the pH within the pH range described above. Examples of suitable buffers are HEPES, and Tris. Divalent cations, such as $Ca^{2+}$, $Mg^{2+}$ or $Mn^{2+}$ may be present. Other compounds such as EDTA and detergents may be added to the assay composition.

The labelled transferase product and/or unreacted labeled second donor may be isolated by conventional isolation techniques suitable for the product, for example, salting out, chromatography, electrophoresis, gel filtration, fractionation, absorption, polyacrylamide gel electrophoresis, agglutination, or combinations thereof. Columns for chromatography may be selected on the basis of the nature of the acceptor substrate and, in particular, the nature of any linker group on the acceptor substrate. For example where the acceptor substrate has a hydrophobic aglycon linker at the reducing end, suitable columns will include those which selectively bind hydrophobic reagents. Examples of columns which are specific for hydrophobic groups include C-18, or C-6 Sep Pak columns (Waters).

The amount of glycosyltransferase in the sample can be calculated from the amount of the isolated labelled transferase product and/or unreacted second sugar donor as measured by methods known in the art. The appropriate method of measuring the labelled material is dependent upon the labelling agent. For example, if the labelling agent is an enzyme, the glycosyltransferase activity may be determined by measuring the enzymatic activity using a proper enzyme substrate for colorimetric, luminescent or fluorescent systems. If the labelling agent is a fluorescent material, glycosyltransferase activity may be determined by measuring fluorescence intensity, and if the labelling agent is a radioactive material, glycosyltransferase activity may be determined by measuring the radioactivity.

Figure 3:
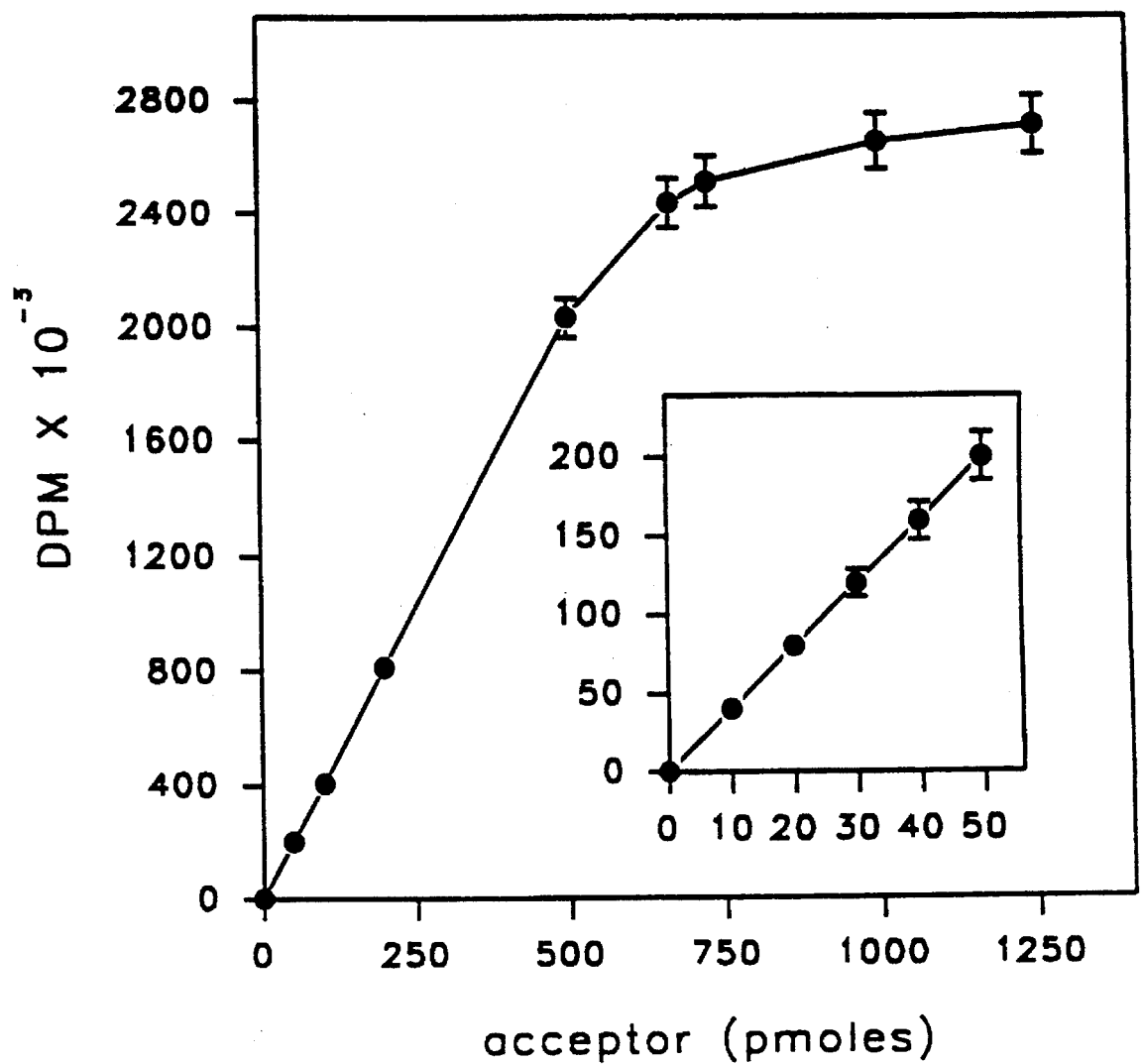
FIG. 3 is a graph showing titration of GlcNAcβ1-2Manα1-6Manβ—O—(CH$_2$)$_8$—COOCH$_3$ as acceptor for bovine β1-4Gal-T. The insert panel shows data on an expanded axis for 0–50 pmoles of acceptor.

Sample measurements will be normalized to the measured specific-activity of the labeled sugar donor in the second reaction (e.g. UDP-Gal), providing moles of sugar transferred in the second reaction. To convert this value to specific activity of the primary transferase reaction, a standard curve is performed for the second reaction to determine efficiency of the second reaction. The efficiency determined over the working range of the second reaction is linear as shown in FIG. 3 of the examples and can be used to calculate the specific activity of the primary transferase reaction (e.g. Table 2, FIG. 6).

The method of the invention can be carried out using a kit for determining glycosyltransferase activity in a sample. The kit may comprise a first sugar donor and an acceptor substrate, the first sugar donor and acceptor substrate being selected such that the sugar portion of the first sugar donor is capable of being transferred to the acceptor substrate in the presence of the glycosyltransferase to be assayed, a second sugar donor having a sugar portion which is labelled with a labelling agent, an enzyme which is capable of transferring the sugar portion from the second sugar donor to the transferase product to produce a labelled transferase product and having a higher affinity for the transferase product compared to the affinity of the glycosyltransferase for the acceptor substrate, and means for detecting the labelling agent activity of the labelled transferase product or unreacted second sugar donor.

The kit may be used to assay for glucosyltransferases or glucosaminyltransferases as described herein for the method of the invention. The first sugar donor, acceptor substrate, second sugar donor and enzyme used in the kit of the invention have been described above in reference to the method of the invention.

The kit contains means for detecting the labelled transferase product or unreacted second sugar donor. Suitable detecting means used in the kit include the use of colorimetric spectrophotometry, fluorescence spectrophotometry, radiometry, chemiluminescence, enzyme labelling, and the like.

Preservatives and/or stabilizers such as bovine serum albumin antibacterial agents such as $NaN_3$ may be used in the kit. The kit may contain other elements such as glycerol or solvents. Examples of suitable solvents are water and PBS. The kit may additionally contain a buffer solution, preferably a buffer solution having a pH of from 5 to 8. The amount of reagents contained in the kit is chosen appropriately depending upon the type of labelling agent or the material to be measured.

In a preferred embodiment, a kit for assaying UDP-GlcNac:Galβ3GalNAc-R β6-N-acetylglucosaminyltransferase activity in a sample, comprises an acceptor substrate comprising Galβ1-3GalNAcα-pNp and a first sugar donor having a GlcNAc sugar portion which is transferred to the acceptor substrate in the presence of UDP-GlcNac:Galβ3GalNAc-R β6-N-acetylglucosaminyltransferase and to produce a transferase product; UDP-Gal wherein Gal is labelled with a labelling agent and β1-4 Gal transferase for transferring labelled Gal to the transferase product to produce a labelled transferase product, and means for detecting the labelling agent activity of the labelled transferase product or unreacted labelled UDP-Gal to determine the UDP-GlcNac:Galβ3GalNAc-R β6-N-acetylglucosaminyltransferase activity.

The method and kit of the invention may be used to assay for glycosyltransferase activity in samples from subjects having conditions associated with aberrant glycosyltransferase activity. Examples of such conditions include cancer, in particular leukemias, fibrosarcomas, and mammary carcinomas, immunodeficiency diseases such as WAS, and lysosomal storage diseases such as type II glycogenosis (Pompe's disease), Gaucher's disease, and Tay-Sachs diseases. The method and kit of the invention may also be used to assay for toxic substances, drugs and their metabolites which are substrates for glucosyltransferases.

The preferred method and kit of the invention to assay core 2 GlcNAc-T allows detection of low levels of enzyme activities and facilitates studies on developmental regulation of core 2 GlcNAc-T. Also the method and kit can be used to measure core 2 GlcNAc-T activity in samples where material is limited, such as lymphocytes from WAS patients. Core 2 GlcNAc-T activity in peripheral lymphocytes of WAS patients is 3 fold higher than that of normal subjects, and this may aid in the diagnosis of WAS children.

Core 2 GlcNAc-T activity appears to be an important rate limiting step in the extension of O-linked oligosaccharides with polylactosamine (i.e., repeating Galβ1-4GlcNAcβ1-3), a structure which has been associated with malignant transformation (Yousefi et al, J. Biol. Chem. 266:1772, 1991). Enzyme activity was also found to be increased following transformation of rat 2 fibroblasts and murine mammary carcinoma cells by activated H-ras (Yousefi, S. et al., J. Biol. Chem. 266:1772, 1991), in human leukemias (Brockhausen, I. et al Cancer Res. 51:1257, 1991). Therefore, the preferred method and kit to assay for core 2 GlcNAc-T activity may also be used in the diagnosis of cancer such as leukemias, fibrosarcomas and mammary carcinomas. The invention will be more fully understood by reference to the following examples. However, these examples are merely intended to illustrate embodiments of the invention and are not to be construed to limit the scope of the invention.

EXAMPLES

The following materials and methods were utilized in the investigations outlined in the examples:

Chemicals

Galβ1-3GalNAcα-pNp and GalNAcα-pNp, H-7, H-8 and H-1004 were purchased from Toronto Research Chemicals, Toronto, Canada, UDP-Gal, UDP-GlcNAc, bovine milk β1-4Gal-T (defined as 5–15 units/mg in the presence of lactalbumin), buffer salts and Triton X-100, cholera toxin, dibutyryl cAMP, 8-bromo-cAMP and phorbol 12-myristate 13-acetate (PMA) and TDA were obtained from Sigma. HPLC grade $KH_2PO_4$ and acetonitrile were obtained from Fisher Scientific. UDP-6-[$^3$H]-galactose (18.9 Ci/mmol) and UDP-6-[$^3$H]-N-acetylglucosamine (26.8 Ci/mmol) were provided by Amersham and NEN, respectively. C18 Sep-Pak were from Millipore-Waters. Actinomycin D and cycloheximide were purchased from Calbiochem. UDP-6-[$^3$H]-galactose (18.9 Ci/mmole) was purchased from Amersham; dimethysulfoxide (DMSO) from BDH; all-trans-retinoic acid and sodium butyrate from Aldrich; α-modified Eagle's minimum essential medium (α-MEM) and fetal calf serum from Gibco.

Cell cultures

Chinese hamster ovary (CHO) cells were as described in Stanley, P. (1984) Ann. Rev. Genet. 18:525. PYS-2 and PAS-5E were derivatives of the F9 teratocarcinoma cells with parietal and visceral endoderm phenotypes, respectively, as generally described in Amos and Lotan (1990) J. Biol. Chem. 265:19192. MDAY-D2 is a metastatic murine lymphoreticular tumor line, described in Kerbel et al (1980) J. Natl. Cancer Inst. 64:1221. Cells were cultured in αMEM supplemented with 10% fetal calf serum and grown at 37° C. in a 95% $O_2$: 5% $CO_2$ humidified atmosphere.

To investigate the effects of differentiating agents on CHO cells some cultures were treated with differentiating agents, including phorbol ester, retinoic acid, DMSO, butyrate and cholera toxin. Sodium butyrate was prepared as a 1M stock solution in phosphate buffered saline and added to cultured cells at final concentration of 2 mM, a concentration which produced optimal stimulation of core 2 GlcNAc-T activity with 90–95% cell viability after 3–4 days. Cell viability was tested by trypan blue dye exclusion. Cholera toxin was dissolved at 1 mg/ml in sterile $H_2O$ and used at 100 ng/ml. All-trans-retinoic acid and PMA were dissolved in DMSO as 1.6 μM stock solutions and used at a final concentration of 1.6 μM. Protein kinase inhibitors H-7, H-8, H-1004 were dissolved in PBS and added to cell cultures at 50 μM as described in Oshima, T. et al, J. Biol. Chem. 266:13621, 1991. Passaged cells were cultured for 24 hours before adding drugs. Doubling times were calculated from the average slopes of growth curves over a 72 hour period. When used as the source of enzyme activity, cell cultures were maintained in logarithmic phase prior to harvesting.

Core 2 GlcNAc-T assays

Cells were washed three times in 0.9% saline and lysed in 0.25% Triton X-100, 0.15M NaCl at 4° C. for 10 minutes. The lysates were adjusted to 8–12 μg/μl protein with lysis solution and used as the source of transferases. The core 2 GlcNAc-T reaction contained 0.1M TES buffer, pH 7.0, 0.125% Triton X-100, 0.1M GlcNAc, 2 mM UDP-GlcNAc, 0.5 μCi UDP-6-[$^3$H]-N-acetylglucosamine, 1 mM Galβ1-3GalNAcα-pNp as acceptor and 20 μl cell lysate (Williams and Schachter, (1980) *J. Biol. Chem.* 255:11247; and Williams et al (1980) *J. Biol. Chem.* 255:11253).

Reactions (total volume 50 μl) were incubated for either 1 or 2 hours at 37° C. and stopped by adding 0.5 ml cold water. Tubes were processed immediately or stored at −20° C. Mixtures were diluted to 5 ml in water, applied to a Sep-Pak C-18 column and washed with 20 ml of $H_2O$. Product was eluted with 5 ml 100% methanol and counted in a β-scintillation counter.

Endogenous glycosyltransferase activities were measured in the absence of acceptor and used to correct activity values determined in the presence of acceptor. The reactions were linear with time of incubation under the conditions used in each assay. Protein concentrations of cell lysates were determined with the bicinchoninic acid reagent supplied by Pierce Chemicals Co. using bovine serum albumin as the standard.

β1-3Gal-T assay

Cell lysates were prepared as described above. The β1-3Gal-T reaction contained 20 mM $MnCl_2$, 0.1M TES pH 6.7, 0.5% Triton X-100, 1.6 mM UDP-Gal, 0.5 μCi UDP-6-[$^3$H]-galactose, 2 mM GalNAcα-pNp as acceptor and 5 μl of cell lysate containing 50–100 μg of protein in a total volume of 50 μl (Schacter et al. (1971) J. Biol. Chem. 246:5321. Samples were diluted to 5 ml in water, applied to a Sep-Pak C-18 column and washed with 20 ml of $H_2O$. Product was eluted with 5 ml 100% methanol and counted in a β-scintillation counter. Endogenous galactosyltransferase activity was measured in the absence of acceptor and used to correct values determined in the presence of acceptor.

Cytosolic cAMP measurements

Cytosolic cAMP levels in CHO cells were determined using a competitive binding assay by Amersham (kit # TRK432). Cells in log phase growth were scraped from tissue culture dishes, thoroughly washed with saline containing 4 mM EDTA, and subjected three times to freeze-thaw cycles. Samples in 200 μl were heated to 100° C. for 2 minutes, followed by centrifugation at 12,000 xg for 10 minutes, and cAMP was measured in the supernatants.

EXAMPLE 1

Single Step Core 2 GlcNAc-T and β1-3Gal-T assays

Core 2 GlcNAc-T was measured in MDAY-D2 cell lysate as a function of reaction time. The reaction was performed at 30° C., or 37° C., using UDP-[$^3$H]GlcNAc and 250 μg of cell lysate protein following the methods described above. The assay showed linear accumulation of product with time at both 30° C. and 37° C. (FIG. 1).

EXAMPLE 2

Coupled Core 2 GlcNAc-T assay

The MDAY-D2 lymphoid tumor cell line has previously been shown to express core 2 GlcNAc-T activity (Yousefi et al (1991) J. Biol. Chem. 266:1772) and was therefore used to establish the coupled assay method, which was carried out as described below.

Cells were washed in 0.9% saline and lysed in 0.25% Triton X-100, 0.15M NaCl at 0° C. Cell lysates were added to reaction mixtures (1:1 v/v) containing 0.2M Tes buffer, pH 7.0, 0.4M. GalNAc, 4 mM UDP-GlcNAc and 2 mM Galβ1-3GalNAcα-pNp, in a total volume of 100 μl. Reactions contained between 1 and 1000 μg of proteins, however when amounts below 15 μg were used, the reaction volume was reduced to 50 μl. Incubations were carried out at 37° C. for either 1 or 2 hours. Reactions were stopped with 500 μl cold water and stored at −20° C. if not processed immediately.

After removing cell debris by centrifugation at 2000 g for 3 minutes, each sample was diluted to 5 ml in water and applied to a C18 Sep-Pak column. Columns were washed with 20 ml water and core 2 GlcNAc-T product was eluted with 4 ml methanol. Methanol was evaporated and the residue taken up in 80 µl of 10 mM Hepes, pH 8.0, 5 µl of 100 mM MnCl$_2$, 2 µCi UDP-$^3$H-Gal and 90 mUnits of bovine milk α1-4Gal-T in 15 µl of 25 mM Hepes pH 8.0, 2.5 mM MnCl$_2$) in a total volume of 100 µl. The β1-4Gal-T reaction was kept at 30° C. for 2 hours and stopped with 500 µl water. The reaction was diluted to 5 ml in H$_2$O, applied to a C18 Sep-Pak and product was eluted with methanol. Methanol was evaporated and the samples resuspended in 150 µl of a 80:20 acetonitrile:water solution. The product, Galβ1-3([$^3$H]Galβ1-4GlcNAcβ1-6)GalNAcα-pNp was further purified on an 7.8×300 mm Ultrahydrogel HPLC column (Millipore-Waters) developed isocratically at 1 ml/min in 80:20 acetonitrile/H$_2$O. Fractions were taken at 1.5 minute intervals and radioactivity counted in a β-counter.

The coupled or two-step core 2 GlcNAc-T assay was performed in series. Core 2 GlcNAc-T reaction product was separated on C18 Sep-Pak in order to reduce endogenous UDP-Gal and Gal-T acceptors prior to the β1-4Gal-T reaction. The recovery of product on the C18 Sep Pac was complete based on pilot studies measuring recovery of standards using absorbance at 303 nm for paranitrophenyl (Zhuang et al (1991) Glycobiology 1:425), and phenol-sulfuric acid assays.

Figure 2:
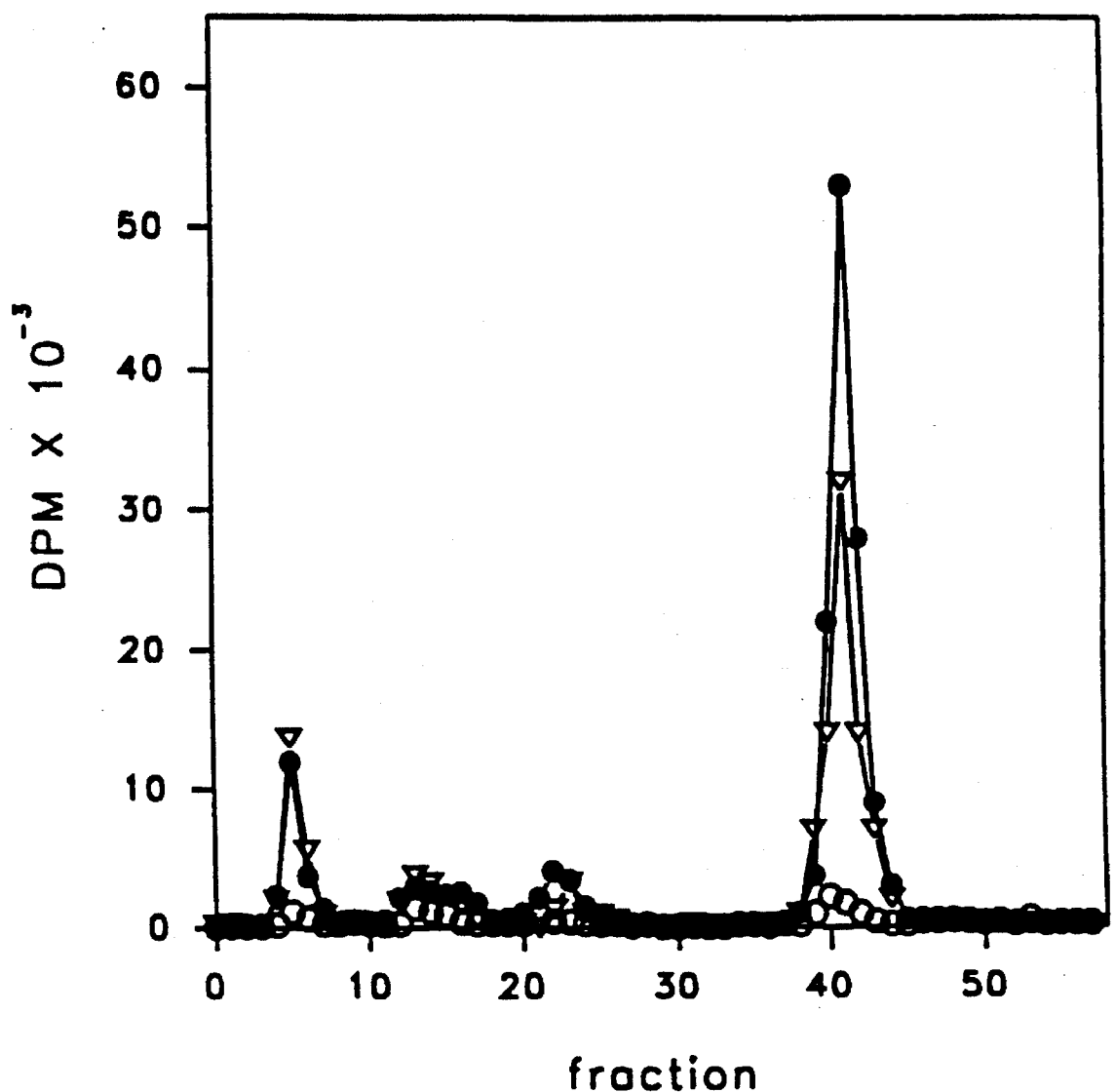
FIG. 2 is a graph showing the separation product, Galβ1-3([$^3$H]Galβ1-4GlcNAcβ1-6)GalNAcα-pNp from the two-step core 2 GlcNAc-T reaction by Ultrahydrogel HPLC for MDAY-D2 cell lysates, (●); CHO cell lysate, (▽); and CHO cell lysate in the absence of acceptor, (○).

Specificity for core 2 GlcNAc-T reaction products was enhanced further by separating the galactosylated product (ie Galβ1-3([$^3$H]Galβ1-4GlcNAcβ1-6)GalNAcα-pNp) on an Ultrahydrogel HPLC column as shown in FIG. 2.

FIG. 2 is a graph showing the separation product, Galβ1-3([$^3$H]Galβ1-4GlcNacβ1-6)GalNAcα-pNp from the two-step core 2 GlcNAc-T reaction by Ultrahydrogel HPLC for 1 µg MDAY-D2 cell lysates, (●); 1 mg CHO cell lysate, (▽); and 1 mg CHO cell lysate in the absence of acceptor, (○). Fractions were 1.5 ml. A Galβ1-3([$^3$H]Galβ1-4GlcNAcβ1-6)GalNAcα-pNp standard comigrated with the peak eluting at fractions 39–45.

The tetrasaccharide reaction product eluted from the HPLC column at 60–70 minutes, coincident with Galβ1-3(Galβ1-4GlcNAcβ1-6)GalNAcα-pNp, a standard previously identified by $^1$H-NMR (Yousefi et al (1991) J. Biol. Chem. 266:1772). Endogenous Gal-T activity which resulted in DPMs eluting coincident with the tetrasaccharide product was low at 2–3,000 DPM, using as much as 1 mg of cell lysate in the assay as shown in FIG. 2.

The second reaction of the coupled assay was characterized using GlcNAcβ1-2Manα1-6Manβ—O(CH$_2$)$_8$COOCH$_3$ as acceptor, 2 µCi of UDP-[$^3$H]Gal (ie. 1.06 µM) and 90 mU of β1-4Gal-T. Incorporation of [$^3$H]Gal into product was directly proportional to acceptor concentration in the range of 0–500 pmoles, and resulted in substitution of 10% of the available acceptor as is shown in FIG. 3. Therefore, with background subtracted, 4,200 DPM=1 pmole of product. With more than 750 pmoles of acceptor, UDP-[$^3$H]Gal was depleted, and 60–65% of the available [$^3$H]Gal was incorporated into product as shown in FIG. 3.

In particular, FIG. 3 shows the titration of GlcNAcβ1-2Manα1-6Manβ—O—(CH$_2$)$_8$—COOCH$_3$ as acceptor for bovine β1-4Gal-T. The reactions were carried out generally as described above and contained 2 µCi of UDP-[$^3$H]Gal, 90 mU of β1-4Gal-T and were incubated for 2 hours at 30° C. Reaction product was separated on C18 Sep-Pak, eluted with methanol and counted in β-counter. Each point in FIG. 3 is mean +/− the range of duplicate determinations. The insert panel shows data on an expanded axis for 0–50 pmoles of acceptor.

With the β1-4Gal-T reaction conditions used, 90 mU of β1-4Gal-T was not rate limiting (FIG. 4A), and the reaction was complete in less than 20 seconds, suggesting that β1-4Gal-T was in excess.

Figure 4:
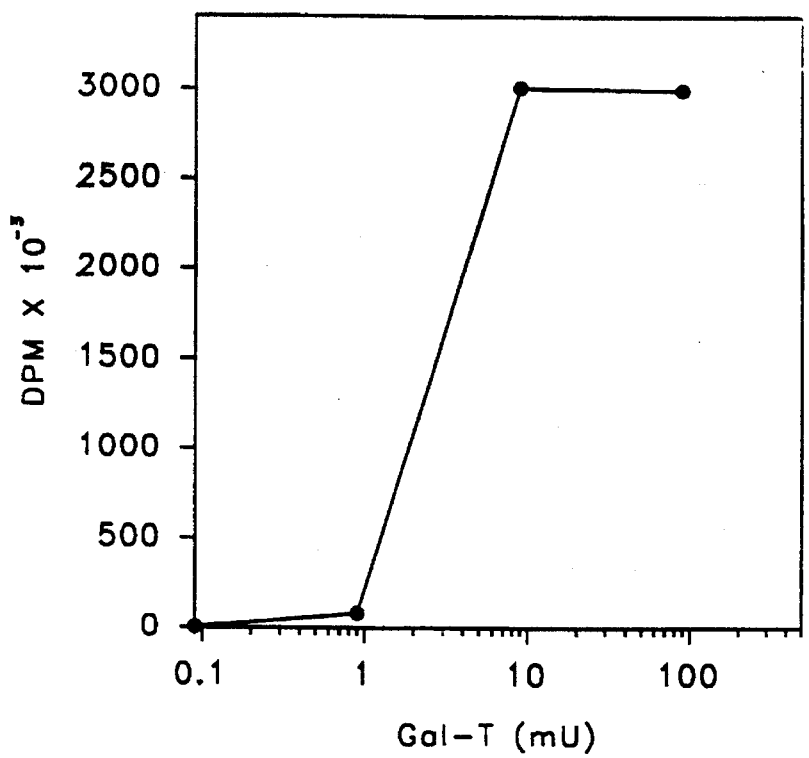
FIG. 4 shows the β1-4Gal-T reaction, 4A is a graph showing titration of the β1-4Gal-T enzyme, and 4B is a graph showing the time course of the β1-4Gal-T reaction.
Figure 4:
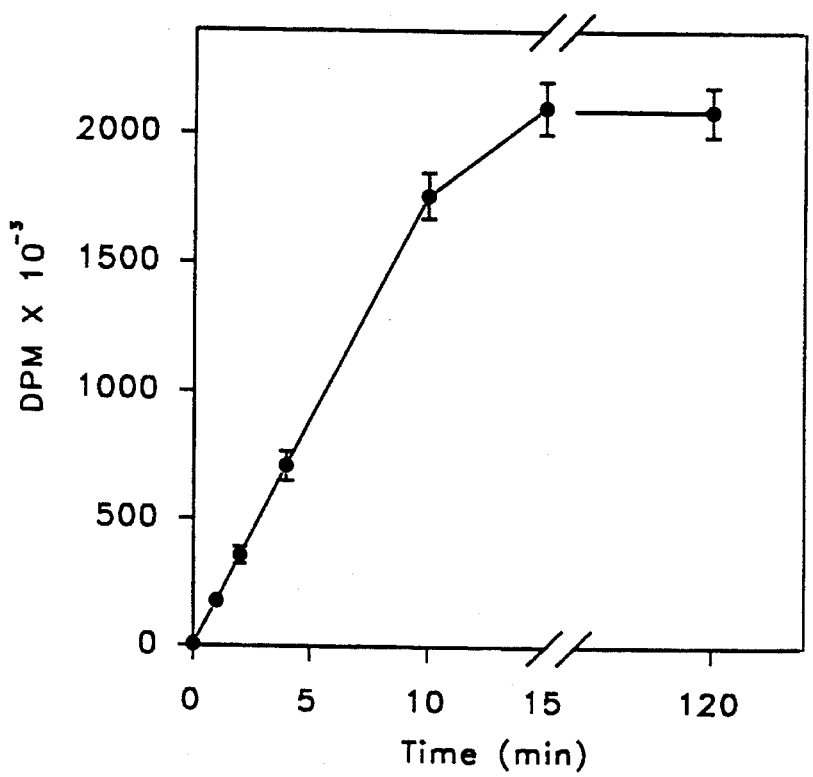

FIG. 4A shows titration of the β1-4Gal-T enzyme. The reactions contained 1500 pmoles of GlcNAcβ1-2Manα1-6Manβ—O—(CH$_2$)$_8$—COOCH$_3$ acceptor (ie. saturating, see FIG. 3), 2 µCi of UDP-[$^3$H]Gal and were incubated for 15 min at 30° C. FIG. 4B shows the time course of the β1-4Gal-T reaction. The reactions contained 500 pmoles of GlcNAcβ1-2Manα1-6Manβ—O—(CH$_2$)$_8$—COOCH$_3$ acceptor (ie subsaturating), 2 µCi of UDP-[$^3$H]Gal and 9 mU of β1-4Gal-T.

From Michaelis-Menten kinetics, the Vi for a two substrate, two product enzyme reactions was calculated as follows (Dixon and Webb (1964) The Enzymes, 2nd Ed., Longmans, London):

$$Vi = \frac{Vmax \frac{S_1 S_2}{Km_1 Km_2}}{1 + \frac{S_1}{Km_1} + \frac{S_2}{Km_2} + \frac{S_1 S_2}{Km_1 Km_2}}$$

Figure 5:
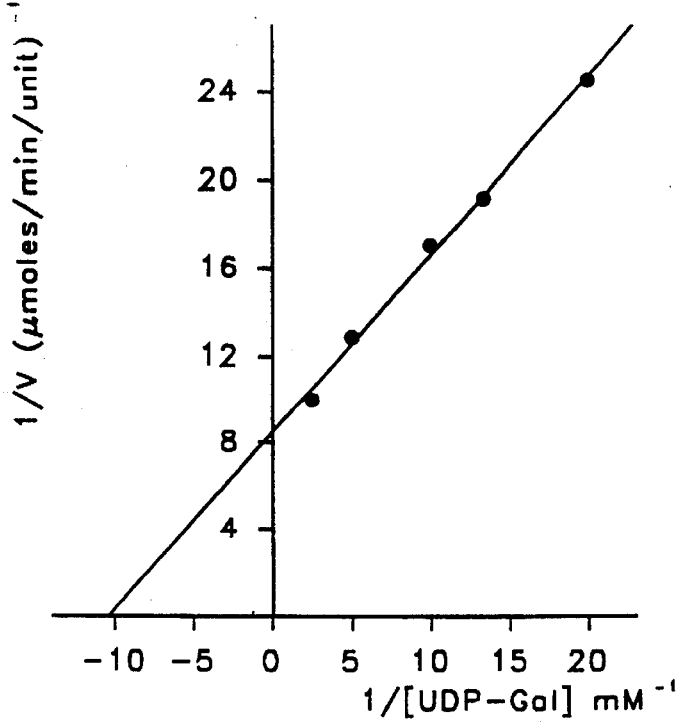
FIG. 5 shows a Lineweaver-Burk plot for β1-4Gal-T activity versus UDP-Gal concentration (A), and for Gal-T activity versus GlcNAcβ1-2Manα1-6Manβ—O—(CH$_2$)$_8$—COOCH$_3$ acceptor concentration (B).
Figure 5:
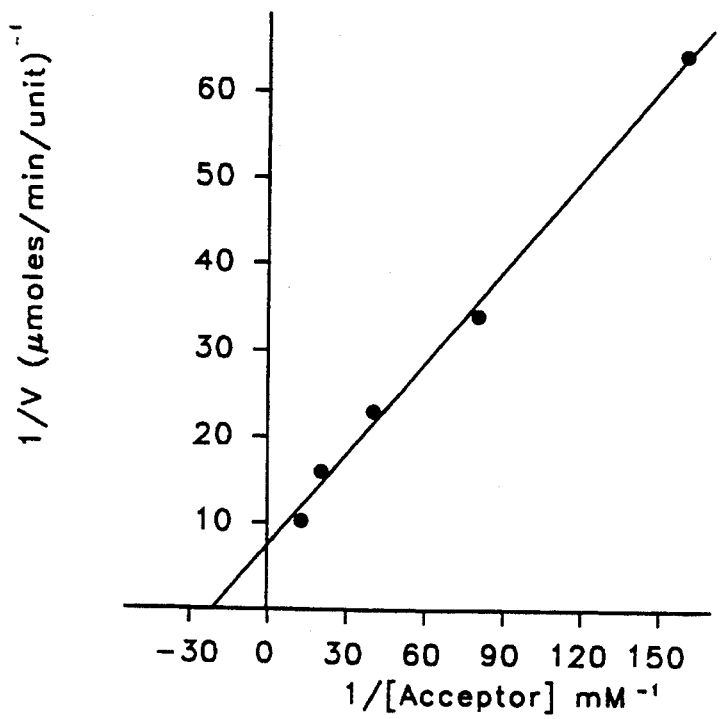

The Km for UDP-Gal, and for acceptor were determined to be 95 µM and 45 µM respectively, and the Vmax was 125 nmoles/min/U (See FIG. 5). FIG. 5 shows Lineweaver-Burk plots for β1-4Gal-T activity versus UDP-Gal concentration; and for Gal-T activity versus GlcNAcβ1-2Manα1-6Manβ—O—(CH$_2$)$_8$—COOCH$_3$ acceptor concentration. Reactions were performed as described above with 1 mU of Gal-T for 5 min at 30° C. In panel A, the reactions contained 1 mM GlcNAcβ1-2Manα1-6Manβ—O—(CH$_2$)$_8$—COOCH$_3$ acceptor. In panel B, the reactions contained 2 mM UDP-Gal.

The above-noted Km and Vmax values were used in the equation above to calculate Vi under the conditions used in FIG. 4B which are similar to the second step of the coupled assay (i.e. 2 µCi of UDP-Gal and subsaturating acceptor). The calculated Vi was 138 pmoles/min/U, while the experimental value determined in FIG. 4B was comparable, at 395 pmoles/min/U. Although the β1-4Gal-T reaction was performed at subsaturating levels of substrate, it appears to be driven rapidly by excess of β1-4Gal-T enzyme. Furthermore, the substrate Km values for β1-4Gal-T were lower than that for the core 2 GlcNAc-T enzyme found in CHO and MDAY-D2 cell lysates (i.e. 0.5 mM for UDP-GlcNAc and 0.3 mM for acceptor), 7 and 5 fold, respectively (Yousefi et al (1991) J. Biol. Chem. 266:1772).

Figure 6:
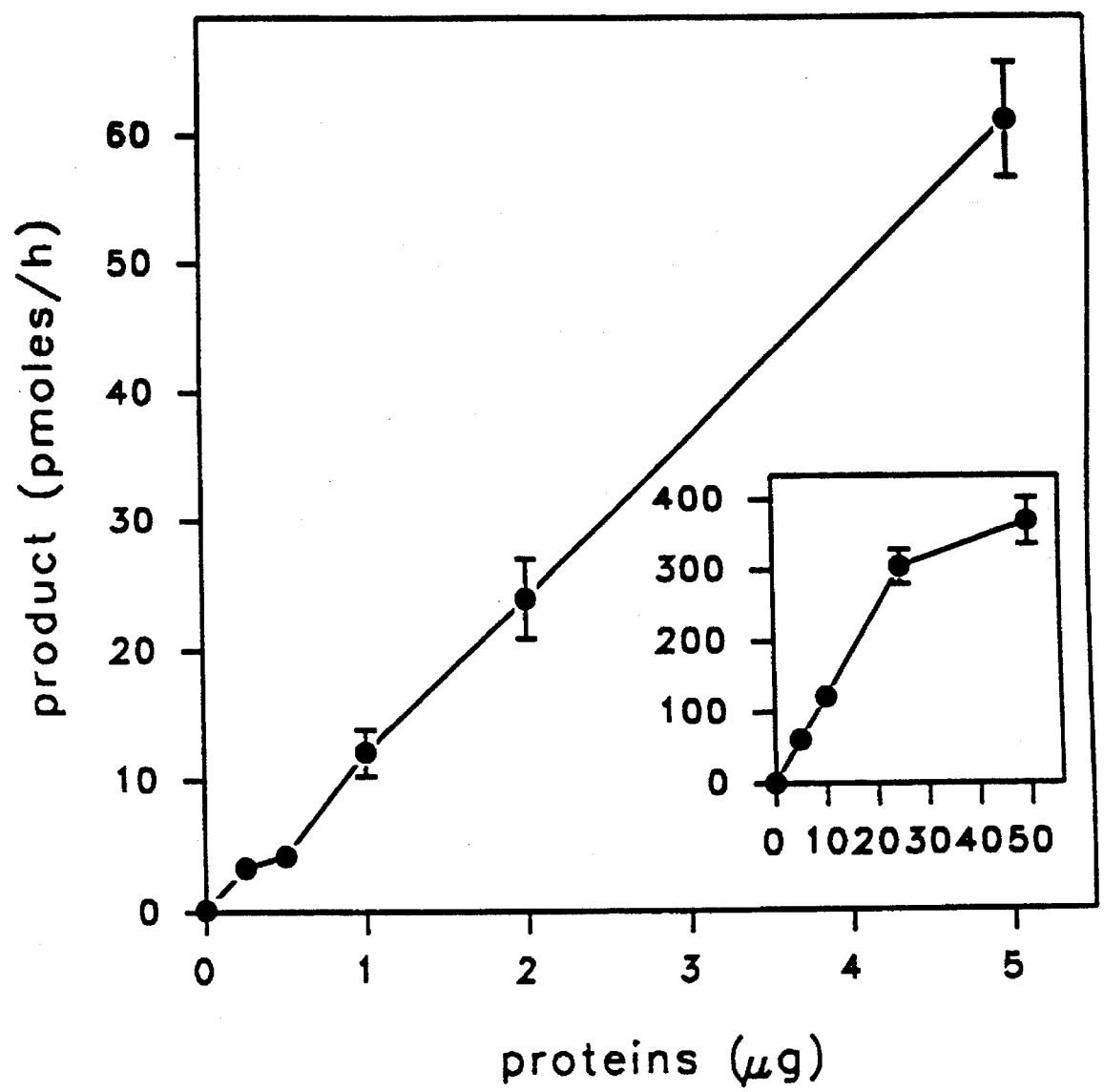
FIG. 6 is a graph showing core 2 GlcNAc-T activity as a function of MDAY-D2 cell lysate added to the primary reaction.

Core 2 GlcNAc-T activity measured in lysates of the MDAY-D2 lymphoma cell line was directly proportional to added lysate in the range of 1 to 25 µg of protein and showed an activity of 12.1 nmoles/mg/h as shown in FIG. 6. FIG. 6 shows core 2 GlcNAc-T activity as a function of MDAY-D2 cell lysate added to the primary reaction. The β1-4Gal-T reactions contained 2 µCi of UDP-[$^3$H]Gal, 90 mU of β1-4Gal-T and were incubated for 2 hours at 30° C. following the methods described above. [$^3$H]Gal-labeled reaction product was quantitated by β-counting following separation by Ultrahydrogel HPLC as shown in FIG. 2. Each point is mean +/− the range of duplicate determinations.

The value for core 2 GlcNAc-T activity measured in lysates of the MDAY-D2 lymphoma cell line compared well with core 2 GlcNAc-T activity measured in the single step assay using UDP-[³H]GlcNAc as is shown in Table 2. Table 2 shows core 2 GlcNAc-T and β1-3Gal-T activities in several cell lines, measured by the coupled assay and the single step assay. As a control for the lysate preparation, β1-3Gal-T activity was found to be present in all preparations. The single step core 2 GlcNAc-T assay was compared to the coupled assay using several cell lines (See Table 2). In cell lines expressing relatively high levels of core 2 GlcNAc-T activity such as MDAY-D2, the enzyme could be measured accurately with only 1 µg of cell lysate protein. Cell lines which appear to lack core 2 GlcNAc-T activity using the single step assay such as CHO and PYS-5E, exhibited activity via the coupled assay. CHO cells showed the lowest activity of the cell lines tested, with a mean ± S.D. of 8.2±0.9 pmoles/mg/h (n=10), demonstrating that activities in the range of 1–10 pmoles/mg/h can be accurately measured with the coupled assay of the invention.

EXAMPLE 3

Regulation of Core 2 GlcNAc-T in CHO Cells CHO cells were exposed to chemical differentiation agents and monitored for induction of core 2 GlcNAc-T activity as described below.

A. Core 2 GlcNAc-T expression in CHO cells treated with differentiating agents.

Core 2 GlcNAc-T activity was observed to be low but measurable in CHO cells using the two-step coupled assay of the invention employing β1-4Gal-T (see Example 2). During the course of experiments in which CHO cells were transfected with DNA using the DEAE-dextran/DMSO shock transfection procedure (Lopata, M. A. et al, 1984, Nucleic Acids Res. 12:5707) a selective increase in core 2 GlcNAc-T was observed after 65–72 hours. Further analysis revealed that the reagents used in the transfection procedure increased core 2 activity 3–4 fold in CHO cells, and induced morphological changes similar to that previously reported for retro-differentiation of CHO cells by sodium butyrate (Storrie, B. et al, 1978) J. Cell Physiol. 94:69; and Milhaud, P. et al, 1980, J. Cell Physiol 104:163).

Figure 7:
FIG. 7 is a photomicrograph showing cell morphology of CHO cells which were (A) untreated, (B) treated with butyrate and (C) treated with cholera toxin.

Core 2 GlcNAc-T activity and cell proliferation rates were measured in CHO cells treated with agents known to induce differentiation (Table 1). DMSO, cholera toxin and butyrate treated cells showed changes in cell morphology (FIG. 7), and increased cell doubling times relative to untreated cells (25–27 hours and 12.5 hours, respectively) (Table 3). FIG. 7 shows the cell morphology of butyrate and butyrate+cholera toxin treated CHO cells as follows: A) untreated cells, B) cells grown for 65 hours in the presence of 2 mM butyrate and C) cells grown for 4 hours in the presence of 100 ng/ml cholera toxin. Only butyrate induced core 2 GlcNAc-T activity, raising enzyme activity in cell lysates 16 fold after 24 hours. Furthermore, induction of glycosyltransferase activity appeared to be selective, as the activity of β1-3Gal-T showed a relatively small increase (i.e., 2–3 times) after 24 h of butyrate treatment. β1-3Gal-T declined to control values by 3–4 days, while core 2 GlcNAc-T activity in butyrate-treated cells remained 10–20 times greater than controls (Table 3, FIG. 8). Cells were incubated with 2 mM butyrate for periods of up to 108 hours, and core 2 GlcNAc-T, ○; and β1-3Gal-T, ●; activities were measured in parallel as described in above.

Cells treated simultaneously with butyrate and cholera toxin exhibited a 30 fold increase in core 2 GlcNAc-T activity after 24 hours which declined to values observed with butyrate-treatment alone (Table 3) by 48–73 hours. Neither cholera toxin alone, retinoic acid, DMSO nor PMA had any effect on core 2 GlcNAc-T activity in CHO cells. This suggests that the butyrate-induced increase in core 2 GlcNAc-T activity is not directly associated with slower cell growth, but may be associated with lineage-specific differentiation. Although the morphology of butyrate-treated CHO cells differs from that of cholera toxin-treated cells (FIGS. 7B, 7C), it is not clear whether these agents induce specific cell lineages.

B. Sodium butyrate treatment causes a biphasic increase in core 2 GlcNAc-T activity in CHO cells.

Figure 8:
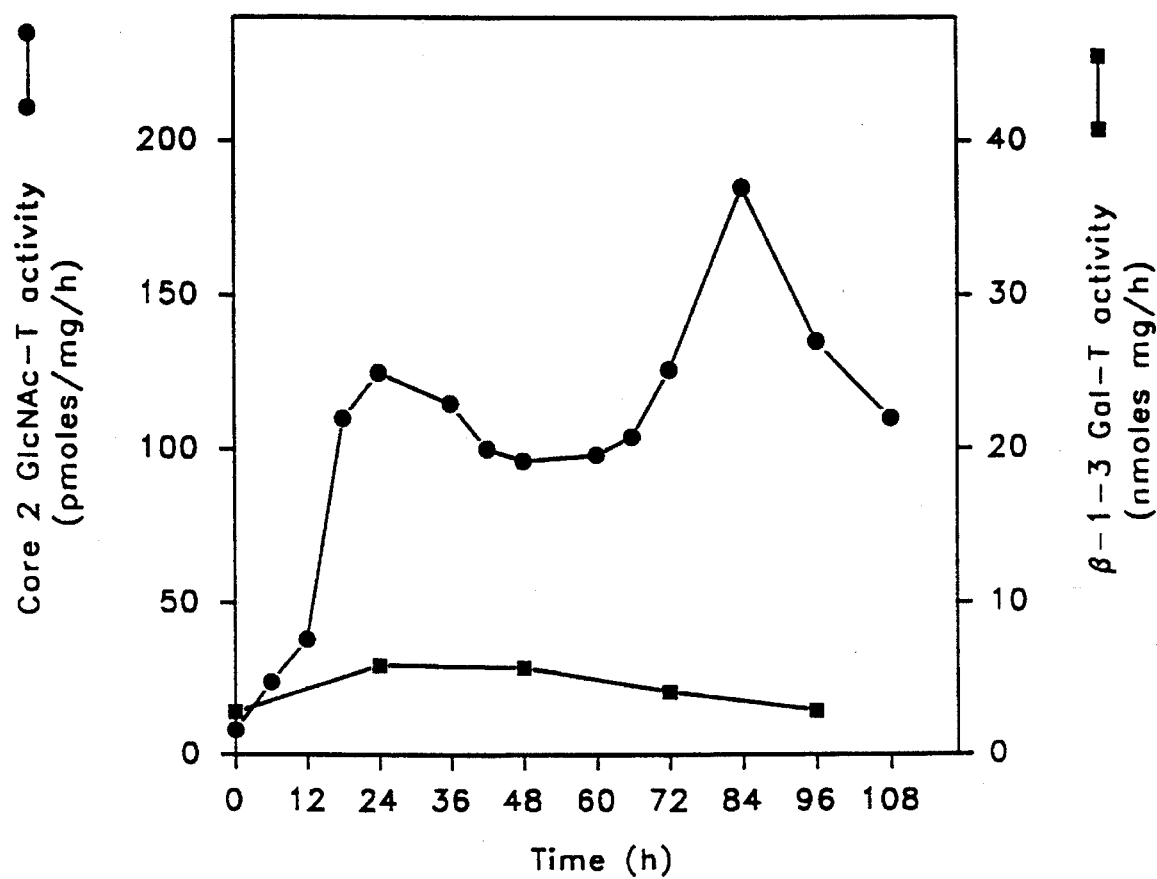
FIG. 8 is a graph showing Core 2 GlcNAc-T activity (●), and β-1-3-Gal-T activity (■) in CHO cells at various times after butyrate-treatment.
Figure 9:
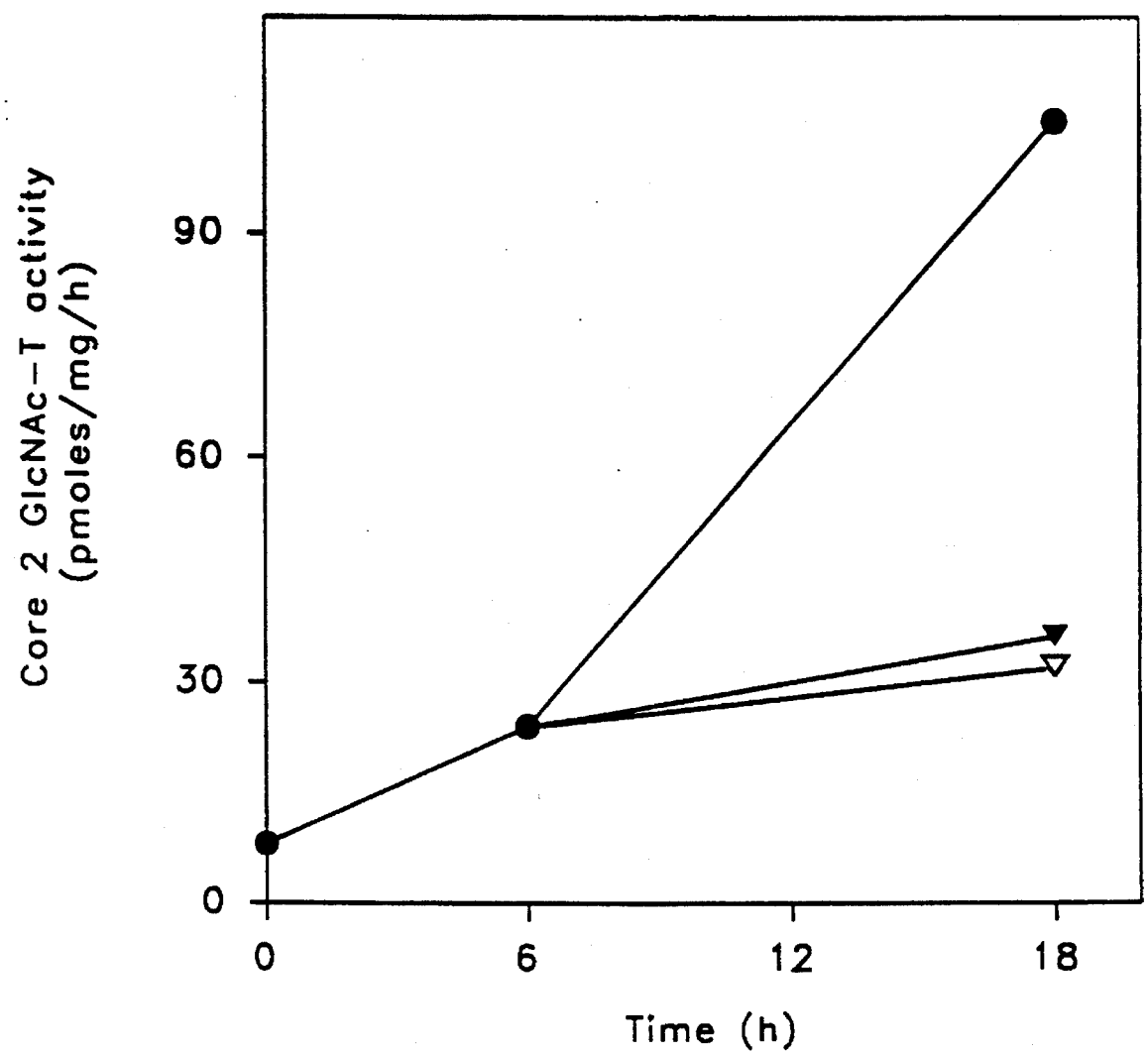
FIG. 9 is a graph showing the induction of core 2 GlcNAc-T activity by butyrate, with no inhibitors (○), or in the presence of actinomycin D (▼), or cycloheximide (▽).

A more detailed time course for core 2 GlcNAc-T induction by butyrate showed a biphasic response (FIG. 8). After 6 hours of butyrate-treatment, enzyme activity increased 2.5 fold, and reached a maximum of 16 fold at 24 hours. A second peak, approximately 45% higher than the 24 hours peak was attained at 84 hours (FIG. 8). The activity of β1-3 Gal-T increased approximately 2 fold after 24 hours of butyrate-treatment and declined to control levels by 72 hours. To determine whether the initial peak of core 2 GlcNAc-T activity occurring 18–24 hours after butyrate treatment required de novo mRNA and protein synthesis, cells were treated with the inhibitors actinomycin D and cycloheximide, respectively, for the period 6 to 18 hours after 2 mM butyrate addition. As shown in FIG. 9, induction of enzyme activity was blocked by these inhibitors suggesting that both de novo transcription and translation is necessary for core 2 GlcNAc-T induction by butyrate. FIG. 9 shows the effects of RNA or protein synthesis inhibitors on induction of core 2 GlcNAc-T activity by butyrate. CHO cells were cultured in the presence of 2 mM Na-butyrate for 6 hours. Incubations were then continued for a further 12 hours in the same medium with no inhibitors (○) or supplemented with 1 µM actinomycin D (▽) or 5 µg/ml cycloheximide (▼).

C. cAMP-mediated induction of core 2 GlcNAc-T activity in CHO cells.

Figure 10:
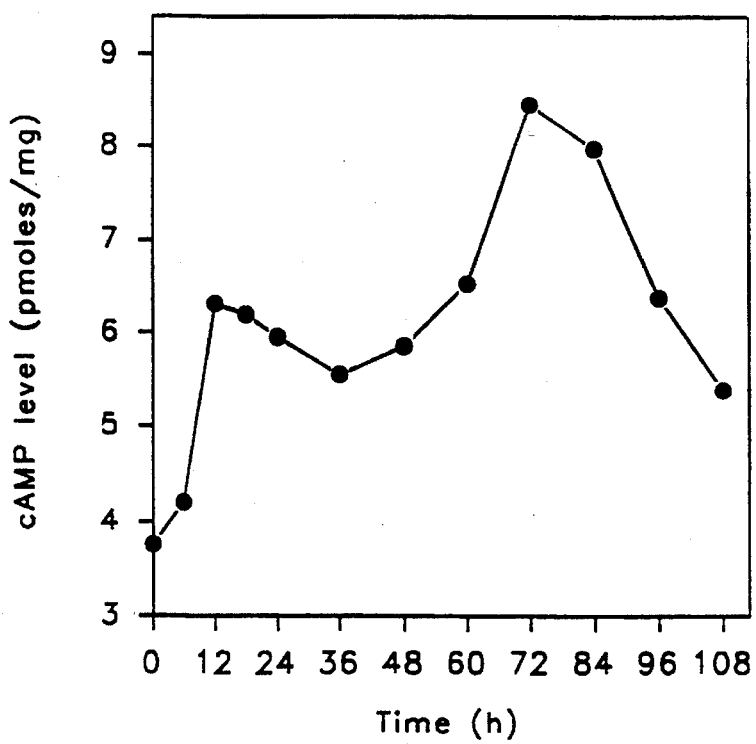
FIG. 10 shows cAMP levels in CHO cells treated with butyrate (A), or with Na-butyrate+cholera toxin (▽) or cholera toxin alone (▼) (B).
Figure 10:
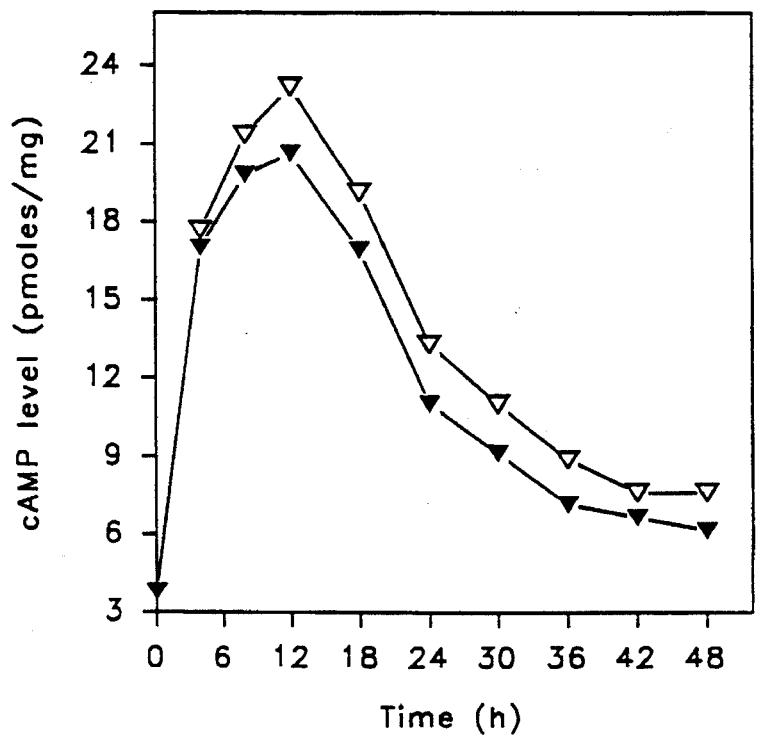

Previous studies have shown that butyrate treatment increases intracellular cAMP levels in CHO cells (Storrie, B. et al, 1978, J. Cell Physiol. 94:69.) and this is confirmed in FIG. 10. FIG. 10 shows cAMP levels in butyrate and cholera toxin CHO cells as follows: A) CHO cells grown in the presence of 2 mM butyrate for up to 108 hours; B) cells grown in the presence of 2 mM Na-butyrate+100 ng/ml cholera toxin (▽) or 100 ng/ml cholera toxin alone (▼). At the indicated times, cell extracts were prepared and intracellular cAMP levels assayed as described above.

Figure 11:
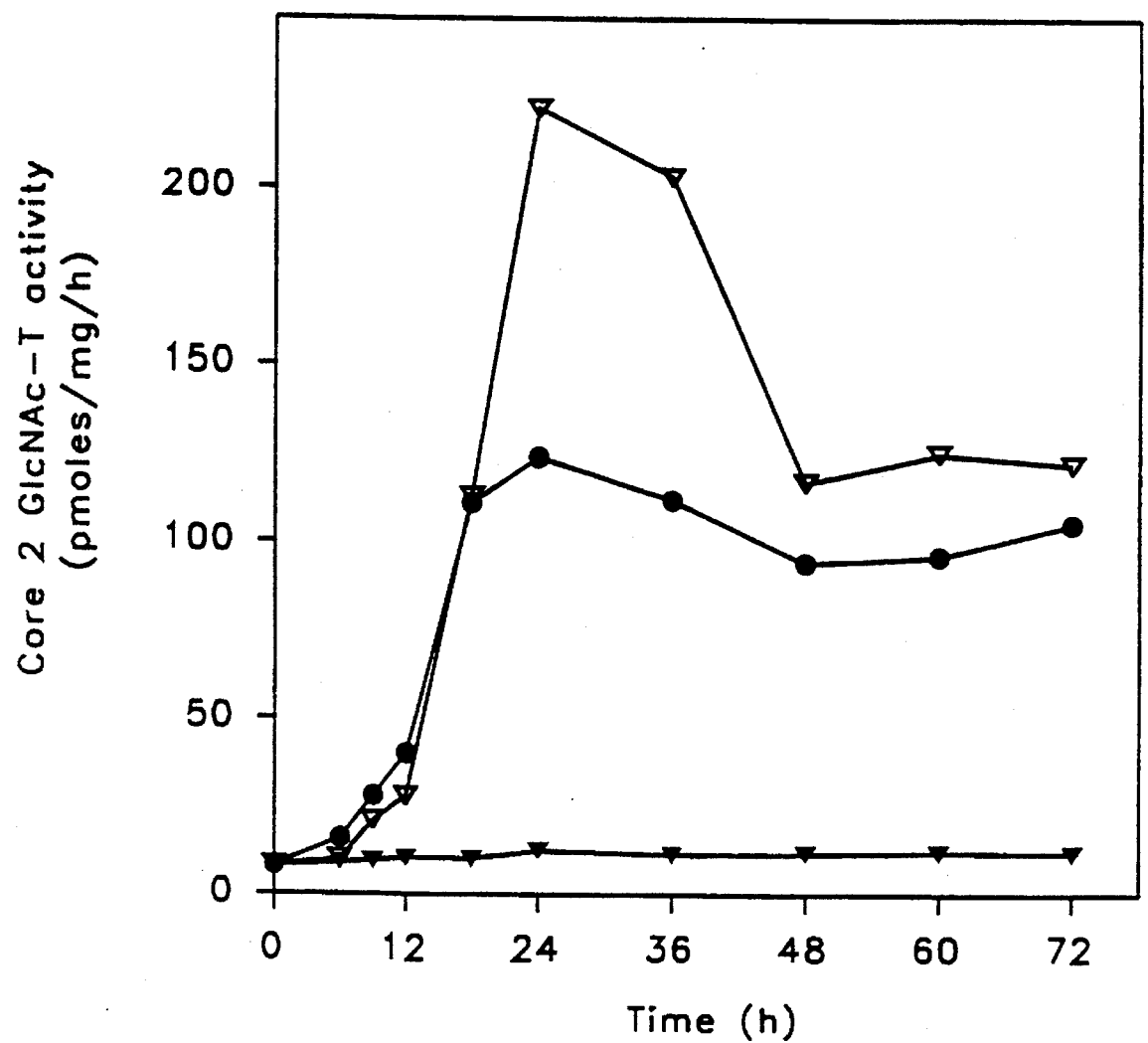
FIG. 11 is a graph showing time-course comparison of core 2 GlcNAc-T activity in butyrate (○), cholera toxin (▼), or butyrate+cholera toxin (▽), treated CHO cells.

Elevated cAMP levels alone, were not sufficient to induce core 2 GlcNAc-T activity, since cholera toxin (Table 3), dibutyryl-cAMP and 8-bromo-cAMP failed to induce enzyme activity. It is possible that in CHO cells induction of core 2 GlcNAc-T by butyrate requires gene transcription, followed by cAMP-dependent protein phosphorylation. In this regard, the time course profile for butyrate induced increases in cAMP was strikingly similar to that of core 2 GlcNAc-T induction; with a first peak at 12 hours and a second at 72 hours (FIG. 10A). Furthermore, raising intracellular cAMP levels in butyrate-treated CHO cells by the addition of cholera toxin (see FIG. 10B), enhanced core 2 GlcNAc-T activity by 80%, from 130 to 223 pmoles/mg/h at 24 h (FIG. 11). FIG. 11 shows a time-course comparison of core 2 GlcNAc-T activity in butyrate, cholera toxin, and butyrate+cholera toxin treated CHO cells. Cell cultures were grown in the presence of 2 mM butyrate (●), 2 mM Na-butyrate+100 ng/ml cholera toxin (▼), or 100 ng/ml cholera toxin (▼) for up to 72 hours. Cells were harvested at various time points and enzyme activity was measured as described above. Similar increases in core 2 GlcNAc-T expression were observed when 1.5 mM dibutyryl cAMP and 1.5 mM 8-bromo-cAMP were added to butyrate-treated cells.

Figure 12:
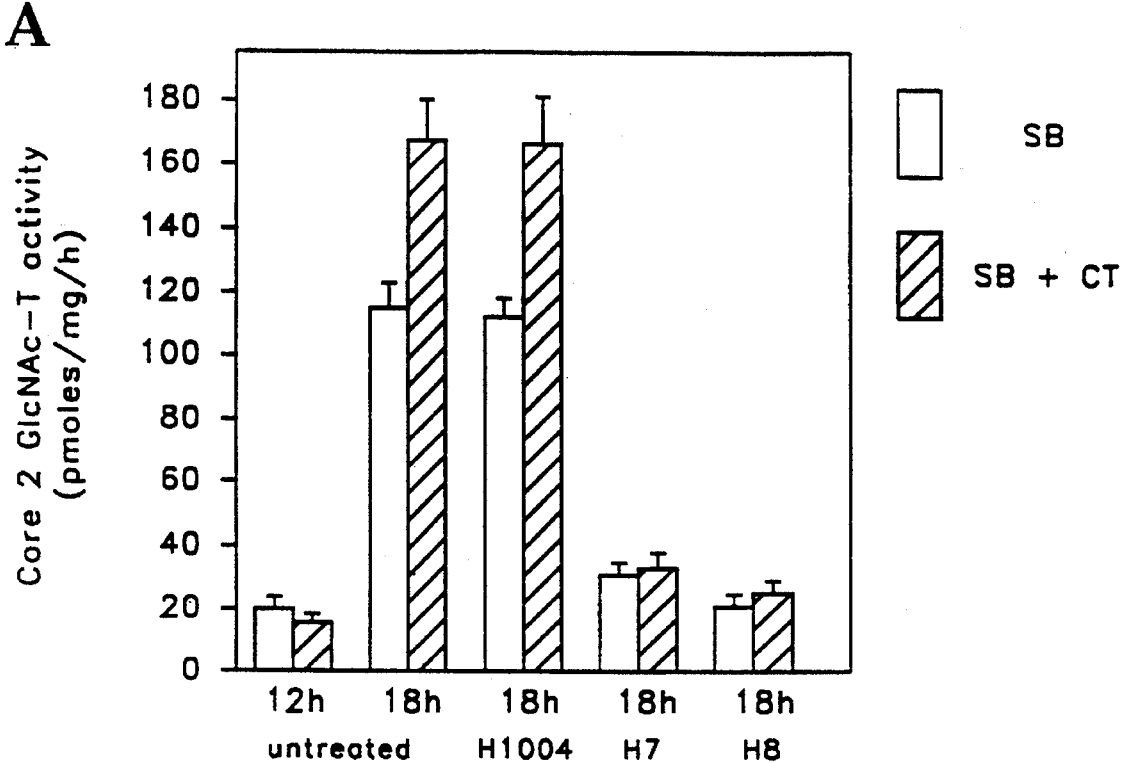
FIG. 12 shows the effects of protein kinase inhibitors H7 and H8 on induction of core 2 GlcNAc-T activity by butyrate, 12A shows cells treated with butyrate (SB) or butyrate+cholera toxin (SB+CT) and H-7, H-8 or H-1004 and 12B shows cells treated with butyrate+cholera toxin and H-8.
Figure 12:
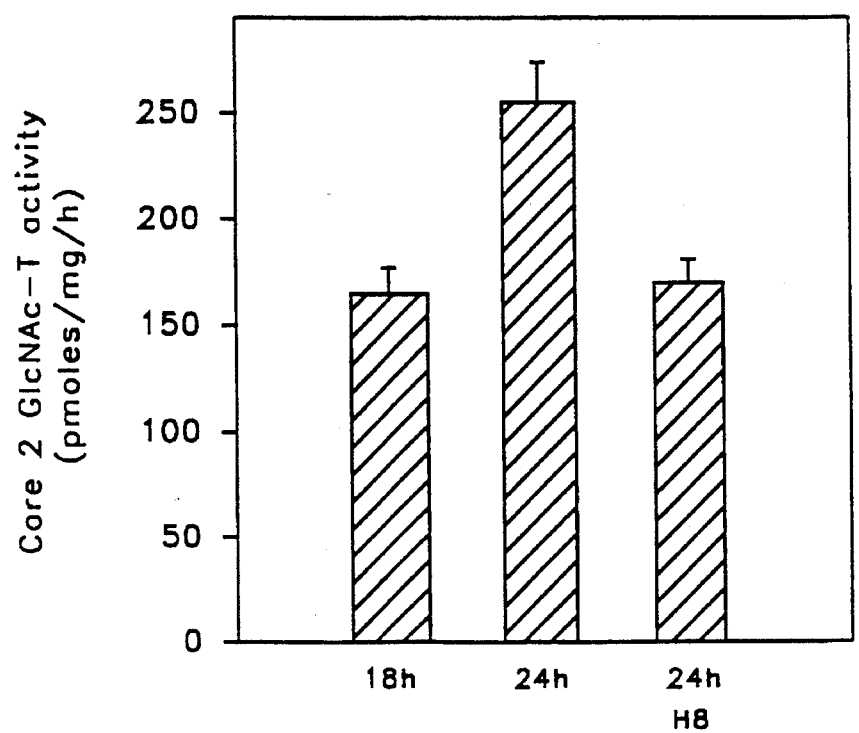

To determine whether inductions of core 2 GlcNAc-T activity by butyrate and butyrate+cholera toxin were dependent upon the action of protein kinases, cells were treated with the kinase inhibitors H-7 and H-8 during butyrate induction (FIG. 12).

FIG. 12 shows the effects of protein kinase inhibitors H-7 and H-8 on induction of core 2 GlcNAc-T activity by butyrate. FIG. 12A) shows CHO cells which were grown in the presence of 2 mM butyrate (SB) or 2 mM butyrate+100 ng/ml cholera toxin (SB+CT) for 12 hours and then cultured for a further 6 hours with or without the addition of H-7, H-8 or H-1004 to a final concentration of 50 μM. FIG. 12B) shows CHO cells which were grown for 18 hours in the presence of 2 mM butyrate+100 ng/ml cholera toxin and then cultured for a further 6 hours with or without 50 μM of H-8. Core 2 GlcNAc-T activity was measured as described above.

H-7 and H-8 are relatively selective inhibitors of $Ca^{++}$-dependent and cAMP-dependent protein kinases, respectively, in cell-free assays, with selectivity based on $IC_{50}$ in the 1–10 μM range (Hidaka, H., et al, 1984, Biochem 23:5036). However, when added to cell cultures intracellular concentrations are difficult to monitor and therefore the levels of inhibitor used in the present experiments (i.e., 50 μM) cannot be considered specific for protein kinase A or C. Induction of core 2 GlcNAc-T activity was reduced approximately 90% by a 6 hour exposure to either inhibitor, whether applied 12 or 18 hours after treatment with butyrate or butyrate+cholera (FIGS. 12A and B). H-1004, an inactive analogue of H-7, had no effect. These data suggest that protein phosphorylation, probably cAMP-dependent, is required for induction of core 2 GlcNAc-T activity during the 12–24 hours period after the addition of butyrate to the cultures.

To determine whether core 2 GlcNAc-T activity could be stimulated in cell lysates by protein kinase A, detergent lysed cell membranes were pre-incubated for 20 minutes with the catalytic subunit of protein kinase A and core 2 GlcNAc-T activity was measured (Table 4). Preincubation of lysates from untreated CHO cells with the kinase enhanced core 2 GlcNAc-T activity by 70%, but did not augment the higher levels observed in butyrate or butyrate+cholera-toxin treated cells.

D. Kinetics of core 2 GlcNAc-T enzyme activity in CHO cells and in cells treated with sodium butyrate+cholera toxin.

Figure 13:
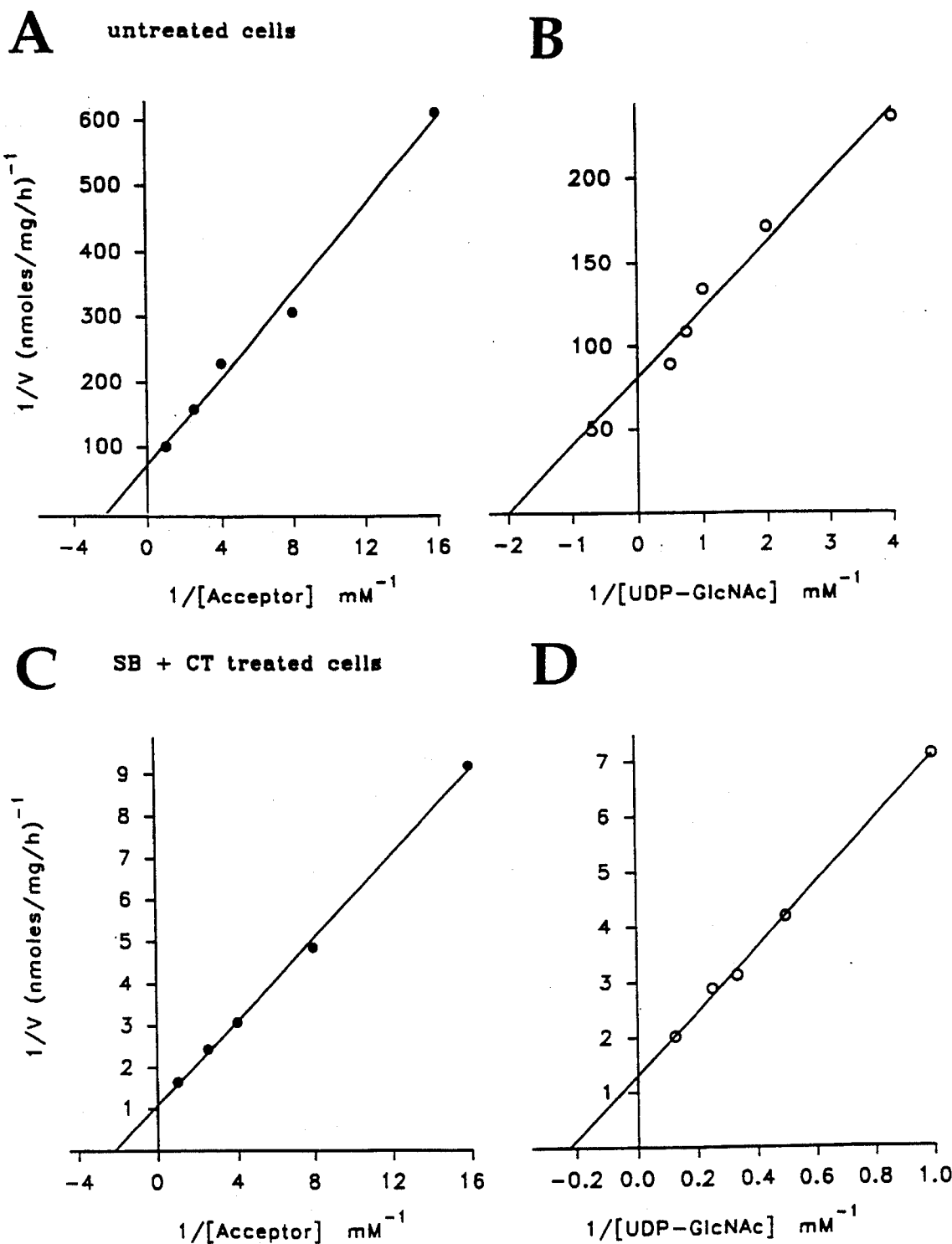
FIG. 13 shows the kinetic analysis of core 2 GlcNAc-T activity. Double reciprocal plots for titrations of the substrates Galβ1-3GalNAcα-pNp (A,C); and UDP-GlcNAc (B,D); in the core 2 GlcNAc-T reaction. (A,B) are untreated CHO cells; C,D are CHO cells cultured in the presence of Na-butyrate+cholera toxin (SB+CT).

The induction of core 2 GlcNAc-T in CHO cells may involve phosphorylation of the enzyme which could result in a change in its catalytic parameters. The apparent Km values for the two substrates, UDP-GlcNAc and the acceptor Galβ1-3GalNAcα-pNp, in lysates of untreated and butyrate+cholera toxin treated CHO cells were determined and are shown in FIG. 13. FIG. 13 shows a kinetic analysis of core 2 GlcNAc-T activity. Double reciprocal plots for titrations of the substrates Galβ1-3GalNAcα-pNp (A,C); and UDP-GlcNAc (B,D); in the core 2 GlcNAc-T reaction. (A,B) are untreated CHO cells; C,D are CHO cells cultured for 24 hours in the presence of 2 mM Na-butyrate+100 ng/ml cholera toxin (SB+CT). Km values for the substrates of core 2 GlcNAc-T from untreated cells were determined using A) 0.063–1 mM acceptor Galβ1-3GalNAcα-pNp; and B) 2 mM UDP-GlcNAc or 0.25–2.0 mM UDP-GlcNAc and 1 mM Galβ1-3GalNAcα-pNp. Km values for the substrates of core 2 GlcNAc-T from cells treated with SB+CT were determined using C), 0.063–1 mM acceptor Galβ1-3GalNAcα-pNp and 10 mM UDP-GlcNAc; D), 1 mM acceptor Galβ1-3GalNAcα-pNp and 1–8 mM UDP-GlcNAc.

The results show that core 2 GlcNAc-T from both sources exhibits similar, apparent Km values for the synthetic acceptor; 0.43 mM in untreated CHO cells, and 0.47 mM in treated cells. However, a remarkable increase in the apparent Km values for the sugar-nucleotide was observed; 0.50 mM for untreated CHO cells versus 4.54 mM for butyrate+cholera toxin treated cells. To ensure that increased pyrophosphatase activity in butyrate+cholera toxin-treated cells was not influencing the apparent Km, the amount of UDP-GlcNAc remaining after a 2 hour incubation was determined under standard core 2 GlcNAc-T reaction conditions, but lacking Galβ1-3GalNAcα-pNp acceptor. Radiolabelled UDP-GlcNAc was used in the experiment, and recovery of the sugar nucleotide was monitored by separation on an Ultrahydrogel HPLC column. Separation of reaction mixtures made with lysates from either control or butyrate+cholera toxin-treated cells showed 93–95% of the UDP-GlcNAc remained intact after a 2 hour incubation.

Despite the 9 fold decrease in affinity toward UDP-GlcNAc, the Vmax for core 2 GlcNAc-T in butyrate+cholera toxin treated CHO cells was approximately 80 fold higher than in controls (i.e., 1,000 versus 12.5 pmoles/mg/h, respectively). Using the Km for the sugar-nucleotide, Vmax/Km is 25 for untreated cells and 220 for butyrate+cholera toxin-treated cells, an 8.8-fold increase. The time course and inhibitor studies of core 2 GlcNAc-T activity in CHO cells (Table 3, FIGS. 7–12) were performed with 2 mM UDP-GlcNAc which allows accurate Vmax determinations in untreated CHO cells. Data from FIG. 13 provides an accurate measure of Vmax in butyrate+cholera toxin treated cells.

Cholera toxin, DMSO and sodium butyrate were found to induce cell differentiation as indicated by reductions in cell growth rates and changes in cell morphology. However, only butyrate induced core 2 GlcNAc-T activity, suggesting that elevated activity is not simply a phenomenon associated with reduced cell proliferation in CHO cells, but may be associated with differentiation induced by specific agents. The morphology of butyrate-treated CHO cells differs from that of DMSO and cholera toxin-treated cells, however the differentiated lineages or induced phenotypes by these agents is unknown. Butyrate and other aliphatic short-chain fatty acids are produced by bacterial fermentation in the colon and can be detected in the circulation and these compounds may affect cell differentiation and glycoprotein glycosylation in vivo.

Figure 14:
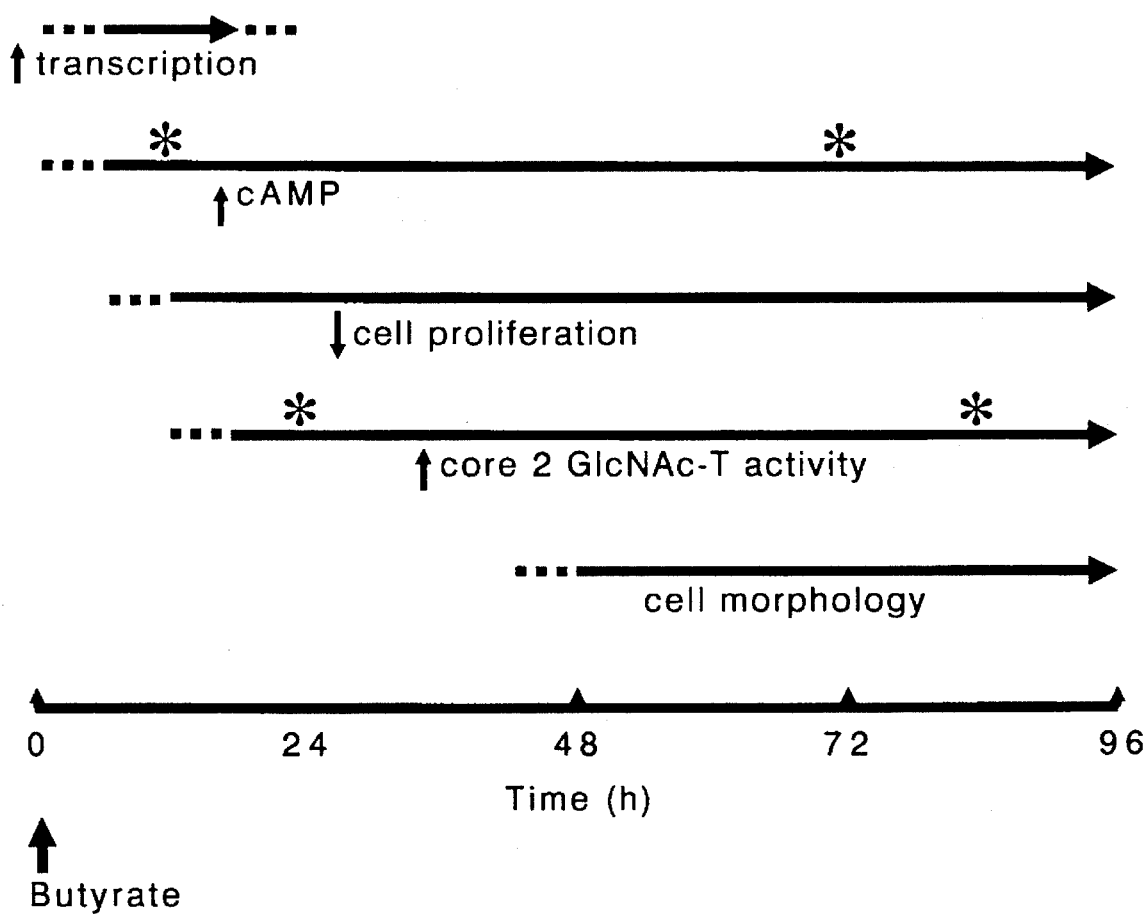
FIG. 14 shows the schematic time course of butyrate induced changes measured in CHO cell. The * indicates local peaks observed in FIGS. 2 & 4.

Actinomycin D and cycloheximide blocked early events (i.e., 6–18 hours) in butyrate-mediated induction of core 2 GlcNAc-T activity, suggesting that transcription of either the transferase gene or regulatory factor(s) is required. Cytosolic cAMP levels also increase during this 6–18 hour period followed by a peak of core 2 GlcNAc-T activity at 24 hours. Protein phosphorylation occurring 12–24 hours after the addition of butyrate was required, as the kinase inhibitors H-7 and H-8 reduced induction of core 2 GlcNAc-T activity by 90% at 24 hours. Furthermore, preincubation of lysates from untreated CHO cells with the catalytic subunit of protein kinase A enhanced core 2 GlcNAc-T activity by 70%, but did not enhance that of butyrate or butyrate+CT treated cells. A schematic time course of events following butyrate-treatment of CHO cells is shown in FIG. 14.

Both H-7 and H-8 blocked induction of core 2 GlcNAc-T activity, and therefore did not allow a distinction between $Ca^{++}$-dependent protein kinases or cAMP-dependent protein kinases. However, other observations suggest that the required protein phosphorylation events may be mediated by a cAMP-dependent protein kinase. The addition of cholera toxin to butyrate-treated CHO cells enhanced both cytosolic cAMP concentrations and core 2 GlcNAc-T activity compared to butyrate-treatment alone, but the protein kinase C activator PMA, alone or with butyrate had no effect. Furthermore, the biphasic time course profiles for butyrate-mediated induction of cytosolic cAMP and core 2 GlcNAc-T activity were strikingly similar; the two peaks of core 2 GlcNAc-T activity at 24 hours and 84 hours were observed 8–12 hours after peaks in cytosolic cAMP. Taken together, these observations suggest that induction of core 2 GlcNAc-T activity in CHO cells by butyrate requires both de novo gene transcription and activation of a cAMP-dependent protein kinase.

Changes in gene expression and, in particular, induction of core 2 GlcNAc-T activity by butyrate are unlikely to be due to increased cAMP alone, since cholera toxin and cAMP analogues failed to stimulate enzyme activity. Therefore, it appears that transcription of a gene product which is a target for a cAMP-dependent protein kinase must be an early event in the induction of core 2 GlcNAc-T activity by butyrate.

Activation of protein kinases may lead to phosphorylation of core 2 GlcNAc-T or factors which regulate the enzyme at the protein level. cAMP binds to the regulatory subunits of the protein kinase A complex and causes dissociation of the active catalytic subunit which can then phosphorylate and activate transcription factors such as CRE and AP-1. For example, CHO mutants which are defective in cAMP-dependent protein kinase activity show loss of stimulation of a cAMP-responsive promoter.

A comparison of the kinetic properties of core 2 GlcNAc-T revealed that the Km for sugar nucleotide substrate has increased approximately 9 fold in butyrate+cholera toxin-treated cells compared to untreated CHO cells. However, no changes in Km for the synthetic acceptor were observed. Despite the high Km for UDP-GlcNAc, Vmax for core 2 GlcNAc-T in treated cells increased 80 fold with respect to untreated cells. Expressed as Vmax/Km, the relative catalytic activity of the enzyme was 8.8 fold greater in treated cells compared to untreated cells. A decrease in the affinity of core 2 GlcNAc-T for UDP-GlcNAc may be due to a post-translational modification of the enzyme such as phosphorylation, or at the gene level, expression of a second core 2 GlcNAc-T gene, or alternate splicing of a single gene transcript. It is possible that acceptors for core 2 GlcNAc-T also affect the sugarnucleotide Km for core 2 GlcNAc-T, which would imply an altered acceptor preference for the enzyme following butyrate treatment in CHO cells.

The carbohydrates of cellular glycoconjugates show structural variation with normal development as well as in disease states, however little is known about the regulation of glycosyltransferases. UDP-GlcNAc:Galβ3GalNAc-R (GlcNAc to GalNAc) β1-6-N-acetylglucosaminyltransferase (i.e., core 2 GlcNAc-T) of the O-linked oligosaccharide pathway is developmentally regulated in human T cells, and changes in its activity have been associated with malignancies and the Wiskott-Aldrich immunodeficiency syndrome. Chinese hamster ovary cells normally express low levels of core 2 GlcNAc-T activity (8–12 pmoles/mg/h) which can be accurately measured with a two step assay employing purified bovine β1-4Gal-T and high-specific activity UDP-[$^3$H]Gal to radiolabel the core 2 reaction product as described herein. CHO cells treated with 2 mM sodium butyrate for 24 h exhibited a 16 fold increase in core 2 GlcNAc-T activity, while several other differentiating agents including dimethylsulfoxide, retinoic acid, phorbol ester and cholera toxin had no effect on activity. The addition of butyrate, cholera toxin or dimethylsulfoxide to CHO cells slowed cell proliferation and induced changes in cell morphology characteristic of cell differentiation. Induction of core 2 GlcNAc-T by butyrate was blocked by actinomycin D and cycloheximide. Butyrate-treatment also elevated cytosolic cAMP levels with a time course which paralleled, but preceded induction of core 2 GlcNAc-T activity by approximately 8 h. Further, raising intracellular cAMP concentrations by exposing butyrate-treated CHO cells to cholera toxin caused an additional 2 fold increase in core 2 GlcNAc-T activity. The protein kinase induction of enzyme activity, while the inactive analogue H1004 had no effect. Core 2 GlcNAc-T showed a change in Km for UDP-GlcNAc, from 0.50 mM in untreated cells to 4.54 mM in butyrate+cholera toxin treated CHO cells, but no changes in Km for the synthetic acceptor, Galβ1-3GalNAcα-para-nitrophenyl. Despite the 9 fold increase in Km for sugar nucleotide, Vmax/Km was 8.8 fold greater in treated compared to untreated cells. These observations suggest that in CHO cells, induction of core 2 GlcNAc-T by butyrate-treatment requires de novo gene transcription/translation, activation of protein kinase(s), and is associated with changes in the kinetic properties of the enzyme.

EXAMPLE 4

Core 2 GlcNAc-T and βGal-T activities in T lymphocytes and platelets from normal individuals and WAS patients.

Peripheral blood from WAS patients and normal individuals was collected into heparinized tubes. Mononuclear cells and platelets were isolated by density gradient centrifugation over Ficol-Paque (Pharmacia LKB Biotechnology Inc.) Platelet and T lymphocytes fractions were prepared generally as described in Higgins et al, J. Biol. Chem. 266:6280, 1991. Core 2 GlcNAc-T and βGal-T activities of T lymphocytes were measured, by the one step conventional assays described herein, before and after stimulation with ant-CD3 antibodies and interleukin-2, following the methods described in Higgins et al, 1991. Core 2 GlcNAc-T and βGal-T activities were measured in resting platelets. The results are shown in Table 5.

FIG 15 shows core 2 GlcNAc-T and βGal-T activities in T lymphocytes and platelets from normal individuals and WAS patients. The values shown in Table 5 are the means ± Standard Deviation of at least three experiments. The activity levels of core 2 GlcNAc-T in resting lymphocytes from WAS patients and healthy donors was quite different. Levels of core 2 GlcNAc-T activity in resting lymphocytes from WAS patients were higher than in resting lymphocytes from healthy donors. The response of the normal and WAS lymphocytes to activation was also quite different. Levels of core 2 GlcNAc-T decreased after activation in WAS patients and increased after activation in healthy donors. The different levels of core 2 GlcNAc-T activity in lymphocytes from healthy donors and WAS patients, and the change in activity following activation, provides a clear basis for diagnosing the occurrence of WAS in a subject.

TABLE 1

Glycosyltransferases Which May Be Assayed Using the Method of the Invention

| Transferase | Substrate |
|---|---|
| UDP-GlcNAc:GalNAc-R β3 N-acetylglucosaminyltransferase | GalNAc |
| UDP-GlcNAc:Manα3-R β2 N-acetylglucosaminyltransferase | Manα1-6(Manα1-3)Man |
| UDP-GlcNAc:Galβ4GlcNAc-R β3 N-acetylglucosaminyltransferase | Galβ1-3GalNAc |
| UDP-GlcNAc:Galβ3GalNAc-R β3 N-acetylglucosaminyltransferase | Galβ1-3GalNAc |
| UDP-GlcNAc:dolichol diphospho N-acetylglucosamine β1-4N-acetylglucosaminyltransferase | dolichol diphospho N-Acetylglucosamine |
| UDP-GlcNAc:Galβ1-3GlcNAc-R β1-3 N-acetylglucosaminyl-transferase | Galβ1-3GlcNAc |
| UDP-GlcNAc:Galβ1-4GlcNAc-Rβ1-6 N-acetylglucosaminyl-transferase | Galβ1-4GlcNAc |
| UDP-GlcNAc:Galβ1-4Glc β-R β1-3 N-acetylglucosaminyl-transferase | Galβ1-4Glc |
| Glucosyltransferases | Natural products, toxins, drugs and their metabolites |

TABLE 2

Core 2 GlcNAc-T and β1-3Gal-T activities in several cell lines.

| Cells | Core 2 GlcNAc-T Coupled assay | Core 2 GlcNAc-T Conventional assay | β3Gal-T |
|---|---|---|---|
|  | (nmoles/mg/h/) | | |
| CHO | 0.0082 | <0.05 | 2.56 |
| MDAY-D2 | 12.10 | 12.26 | 34.70 |
| PYS-2 (parietal) | 8.24 | 8.23 | 9.44 |
| PAS-5E (visceral) | 0.075 | 0.05 | 5.05 |

Glycosyltransferase activities were measured as described in Materials and Methods.

TABLE 3

Glycosyltransferase activities and proliferation of CHO cells in the presence of differentiation agents.

| Duration of Treatment | Core 2 GlcNAc-T (pmoles/mg/h) | | | B-1 Gal-T (nmoles/m/h) | | | Doubling Time (Hours) |
|---|---|---|---|---|---|---|---|
|  | 24 h | 48 h | 72 h | 24 h | 48 h | 72 h |  |
| RA* | 7.1 | 7.7 | 9.0 | 4.9 | 2.0 | 1.5 | 13 |
| RA + TPA | 7.5 | 11.1 | 10.1 | 3.4 | 2.1 | 1.5 | 13 |
| TPA | 7.5 | 10.5 | 8.6 | 2.5 | 1.8 | 2.5 | 13 |
| DMSO | 9.6 | 11.2 | 9.5 | 9.1 | 8.1 | 5.6 | 25 |
| SB | 130.0 | 96.0 | 126.0 | 5.9 | 5.7 | 4.1 | 24 |
| CT | 12.5 | 11.6 | 11.7 | 2.6 | 2.7 | 2.4 | 27 |
| SB + CT | 223.0 | 117.0 | 122.0 | 4.1 | 3.9 | 3.2 | 27 |

Cells were harvested from subconfluent cultures at the time points shown. Viability was >95% as determined by trypan blue dye exclusion. Enzyme activities were measured as described in "Experimental Procedures". Doubling times were calculated from the average slopes of growth curves over a 72 hour period.
Control values for subconfluent cultures of untreated CHO cells were: core 2 GlcNAc-T (pmoles/mg/h) + 8.3 ± 0.9; β1-3 Gal-T.
All data shown are representative of three independent determinations.
*Abbreviations used: RA = 1.6 μM all-trans retinoic acid, TPA = 1.6 μM phorbol 12-myristate 13-acetate, DMSO = 2% dimethylsuphoxide, SB + 2 mM sodium butyrate, CT = 100 ng/ml cholera toxin.

TABLE 4

Stimulation of core 2 GlcNAc-T activity in CHO cell lysates with the catalytic subunit of PKA.

| | core 2 GlcNAc-T[1] (pmoles/mg/h) | | kinase activity[2] (cpm × 10$^{-3}$) | |
|---|---|---|---|---|
|  | kinase − | + | − | + |
| control | 20.0 | 34.2 | 633 | 1680 |
| butyrate | 267.4 | 264.9 | N.D. | N.D. |
| Butyrate + CT | 714.9 | 679.4 | N.D. | N.D. |

[1]·Cells were lysed by freeze-thawing 3 times in 0.1M Tris.HCl pH 7.5, 0.25M sucrose 0.1 mM EDTA. Membranes were pelleted at 20,000 × g and suspended in 10 mM TES pH 7.0, 10 mM MgCl$_2$, 10 mM KF, 1% DMSO, 0.2 mM ATP, 25 mM sucrose, plus 500 units protein kinase A catalytic subunit/0.5 mg of lysate protein; incubated for 20 min at 30° C. followed by addition of the core 2 GlcNAc-T cocktail to give final concentrations of substrates as described in Experimental Procedures.
[2]·$^{32}$Pγ-ATP incorporation into cell lysate proteins over 20 min at 30° C. N.D., not done.

TABLE 5

| | Lymphocytes[2] | | | | Platelets[3] | |
|---|---|---|---|---|---|---|
| | Core 2 GlcNAc-T activity | | β1-3 Gal-T activity | | Core 2 | β1-3Gal-T |
| | Resting | Activated | Resting | Activated | activity | activity |
| Healthy donors | | | | | | |
| AG | 0.41 ± 0.08 | 2.18 ± 0.15 | 29.10 ± 2.18 | 23.15 ± 0.92 | ND | ND |
| BM | 0.73 ± 0.15 | 1.83 ± 0.21 | 20.80 ± 1.32 | 15.65 ± 1.22 | 1.05 ± 0.15 | 12.68 ± 1.20 |
| MM | 0.65 ± 0.09 | 1.85 ± 0.22 | 25.77 ± 1.88 | 29.23 ± 3.13 | 1.60 ± 0.20 | 9.18 ± 0.98 |
| RM | 0.90 ± 0.06 | 1.89 ± 0.10 | 23.12 ± 2.19 | 19.81 ± 1.24 | 1.28 ± 0.09 | 8.36 ± 1.32 |
| MM | 1.00 ± 0.15 | 2.15 ± 0.08 | ND | ND | ND | ND |
| LL | 0.70 ± 0.13 | 1.64 ± 0.11 | 25.76 ± 1.00 | 24.45 ± 2.07 | 1.13 ± 0.12 | 10.04 ± 1.00 |
| DR | 1.01 ± 0.22 | 2.24 ± 0.16 | 17.43 ± 0.89 | 21.94 ± 2.37 | 1.2 ± 0.2 | ND |
| BO | 1.41 ± 0.22 | 2.33 ± 0.19 | 16.154 ± 1.05 | 25.61 ± 1.39 | 1.5 ± 0.1 | ND |
| Wiskott-Aldrich patients (WAS) | | | | | | |
| MO | 2.67 ± 0.16 | 0.83 ± 0.09 | 18.21 ± 0.73 | 23.35 ± 0.75 | 2.79 ± 0.12 | 9.15 ± 1.14 |
| FM | 2.08 ± 0.14 | 0.87 ± 0.13 | 16.54 ± 1.35 | 28.63 ± 2.60 | 2.36 ± 0.04 | 7.33 ± 0.23 |
| TM | 1.93 ± 0.16 | 0.38 ± 0.15 | 17.45 ± 2.34 | 22.89 ± 0.67 | 3.15 ± 0.38 | 9.24 ± 1.50 |
| AC | 2.35 ± 0.15 | 1.05 ± 0.06 | ND | ND | 1.9 ± 0.1 | ND |

TABLE 5-continued

|  | Lymphocytes[2] | | | | Platelets[3] | |
| --- | --- | --- | --- | --- | --- | --- |
|  | Core 2 GlcNAc-T activity | | β1-3 Gal-T activity | | Core 2 | β1-3Gal-T |
|  | Resting | Activated | Resting | Activated | activity | activity |
| HB | 2.04 ± 0.87 | 0.87 ± 0.11 | ND | ND | ND | ND |
| CD | 3.28 ± 0.43 | 0.65 ± 0.13 | 23.21 ± 1.23 | 29.45 ± 2.22 | 2.7 ± 0.2 | ND |
| JR | 2.00 ± 0.17 | 0.78 ± 0.11 | 14.67 ± 0.62 | 15.44 ± 1.77 | 2.2 ± 0.2 | ND |
| JG | 2.10 ± 0.10 | 0.25 ± 0.22 | ND | ND | ND | ND |
| JR | 1.85 ± 0.12 | 0.48 ± 0.09 | 22.35 ± 1.2 | 22.39 ± 1.60 | 2.4 ± 0.3 | ND |

We claim:

1. A method of assaying for a glycosyltransferase in a sample, which comprises the steps of:
   (a) reacting the sample with a first sugar donor and an acceptor substrate which in the presence of a glycosyltransferase in the sample produces a transferase product, the first sugar donor and acceptor substrate being selected such that the sugar from the first sugar donor is capable of being transferred to the acceptor substrate in the presence of the glycosyltransferase to be assayed;
   (b) reacting the transferase product with a second sugar donor having a sugar which is labelled with a labelling agent and a transferase enzyme which is capable of transferring the sugar from the second sugar donor to the transferase product to produce a labelled transferase product and which has a higher affinity for the transferase product compared to the affinity of the glycosyltransferase for the acceptor substrate, and assaying for the labelling agent activity of the labelled transferase product or unreacted second sugar donor.

2. A method as claimed in claim 1 wherein the first sugar donor is a nucleotide sugar donor.

3. A method as claimed in claim 1 wherein the second sugar donor is a nucleotide sugar donor.

4. The method as claimed in claim 1, wherein the acceptor substrate has an oligosaccharide portion and a linker group.

5. A method as claimed in claim 1 wherein the transferase enzyme is β1-4 Gal-T and the second sugar donor is a nucleotide sugar donor comprising Gal labelled with a labelling agent.

6. A method as claimed in claim 5 wherein the second sugar donor is UDP-Gal labeled with a labeling agent.

7. A method as claimed in claim 1 wherein the labelling agent is an enzyme, fluorescent substance, radioactive substance, or chemiluminescent substance.

8. The method as claimed in claim 1, wherein the glycosyltransferase is a glucosyltransferase.

9. The method as claimed in claim 1, wherein the glycosyltransferase is a glucosaminyltransferase glucoaminyltransferase.

10. A method as claimed in claim 9 wherein the glucosaminyltransferase to be assayed is UDP-GlcNac:Galβ3GalNAc-R β6-N-acetylglucosaminyltransferase; UDP-GlcNAc:GalNAc-R β3-N-acetylglucosaminyltransferase; UDP-GlcNAc:α3Man β2-N-acetylglucosaminyltransferase I; UDP-GlcNAc:Gal β4GalNAc-R β3-N-acetylglucosaminyltransferase; UDP-GlcNAc:Galβ3GalNAc-R β3-N-acetylglucosaminyltransferase; UDP-GlcNAc: dolichol diphospho N-acetylglucosamine β1-4 N-acetylglucosaminyltransferase; UDP-GlcNAc:Galβ1-3GlcNAc-R β1-3 N-acetylglucosaminyltransferase; UDP-GlcNAc:Galβ1-4GlcNAc-R β1-6 N-acetylglucosaminyltransferase; or UDP-GlcNAc:Galβ1-4Glc β-R β1-3 N-acetylglucosamimyltransferase.

11. A method as claimed in claim 9 wherein the glucosaminyltransferase to be assayed is UDP-GlcNac:Galβ3GalNAc-R β6-N-acetylglucosaminyltransferase.

12. A method as claimed in claim 11 wherein the acceptor substrate comprises Galβ1-3GalNAcα-pNp.

13. A method as claimed in claim 12 wherein the first sugar donor is UDP-GlcNAc.

14. A kit for assaying for glycosyltransferase activity in a sample comprising a first sugar donor and an acceptor substrate, the first sugar donor and acceptor substrate being selected such that the sugar portion of the first sugar donor is capable of being transferred to the acceptor substrate in the presence of the glycosyltransferase to be assayed to produce a transferase product, a second sugar donor having a sugar portion which is labelled with a labelling agent, a transferase enzyme which is capable of transferring the sugar portion from the second sugar donor to the transferase product to produce a labelled transferase product and which has a higher affinity for the transferase product compared to the affinity of the glycosyltransferase for the acceptor substrate, and means for detecting the labelling agent activity of the labelled second transferase product or unreacted second sugar donor.

15. A kit as claimed in claim 14 wherein the second sugar donor is UDP-Gal labeled with a labeling agent.

16. A kit as claimed in claim 14 wherein the first sugar donor is a nucleotide sugar donor.

17. A kit as claimed in claim 14 wherein the second sugar donor is a nucleotide sugar donor.

18. A kit as claimed in claim 14, wherein the acceptor substrate has an oligosaccharide portion and a linker group.

19. A kit as claimed in claim 14 wherein the enzyme is β1-4 Gal-T and the second sugar donor is a nucleotide sugar donor comprising Gal labelled with a labelling agent.

20. A kit as claimed in claim 14 wherein the labelling agent is an enzyme, radioactive substance, luminescent substance, or chemiluminescent substance.

21. A kit as claimed in claim 14 wherein the glycosyltransferase is a glucosylaminotransferase.

22. A kit as claimed in claim 21 wherein the glucosaminyltransferase to be assayed is UDP-GlcNac:Galβ3GalNAc-R β6-N-acetylglucosaminyltransferase; UDP-GlcNAc:GalNAc-R β3-N-acetylglucosaminyltransferase; UDP-GlcNAc:α3Man β2-N-acetylglucosaminyltransferase I; UDP-GlcNAc:Gal β4GalNAc-R β3-N-acetylglucosaminyltransferase; UDP-GlcNAc:Galβ3GalNAc-R β3-N-acetylglucosaminyltransferase; UDP-GlcNAc: dolichol diphospho N-acetylglucosamine β1-4 N-acetylglucosaminyltransferase; UDP-GlcNAc:Galβ1-3GlcNAc-R β1-3 N-acetylglucosaminyltransferase; UDP-GlcNAc:Galβ1-4GlcNAc-R β1-6 N-acetylglucosaminyltransferase; or UDP-GlcNAc:Galβ1-4Glc β-R β1-3 N-acetylglucosaminyltransferase.

23. A kit for assaying UDP-GlcNac:Galβ3GalNAc-R β6-N-acetylglucosaminyltransferase activity in a sample, comprising an acceptor substrate comprising Galβ1-3GalNAcα-pNp and a first sugar donor having a GlcNAc sugar portion which is transferred to the acceptor substrate in the presence of UDP-GlcNac:Galβ3GalNAc-R β6-N-acetylglucosaminyltransferase to produce a transferase product; UDP-Gal wherein Gal is labelled with a labelling agent and β1-4 Gal transferase for transferring labelled Gal to the transferase product to produce a labelled transferase product, and means for detecting the labelling agent activity of the labelled transferase product or unreacted labelled UDP-Gal to determine the UDP-GlcNac:Galβ3GalNAc-R β6-N-acetylglucosaminyltransferase activity.

24. The kit as claimed in claim 23 further comprising means for comparing the UDP-GlcNac:Galβ3GalNAc-R β6-N-acetylglucosaminyltransferase activity in samples from a normal patient and a patient with a condition associated with aberrant UDP-GlcNac:Galβ3GalNAc-R β6-N-acetylglucosaminyltransferase activity.

25. A kit as claimed in claim 24 wherein the condition is Wiskott-Aldrich immunodeficiency syndrome (WAS).

26. A kit as claimed in claim 25 wherein the sample consists of peripheral blood.

27. A kit as claimed in claim 25 wherein the sample consists of peripheral lymphocytes or platelets.

28. A kit as claimed in claim 26 wherein the condition is cancer.

* * * * *